United States Patent
Weiss et al.

(10) Patent No.: US 12,331,298 B2
(45) Date of Patent: Jun. 17, 2025

(54) PHOSPHORYLATION-BASED miRNA SENSOR

(71) Applicant: Massachusetts Institute of Technology, Cambridge, MA (US)

(72) Inventors: Ron Weiss, Newton, MA (US); Ross D. Jones, Cambridge, MA (US); Jin Huh, Watertown, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 253 days.

(21) Appl. No.: 17/811,593

(22) Filed: Jul. 11, 2022

(65) Prior Publication Data

US 2023/0235334 A1  Jul. 27, 2023

Related U.S. Application Data

(63) Continuation of application No. 16/528,772, filed on Aug. 1, 2019, now abandoned.

(60) Provisional application No. 62/713,160, filed on Aug. 1, 2018.

(51) Int. Cl.
*C12N 15/52* (2006.01)
*C12Q 1/6876* (2018.01)

(52) U.S. Cl.
CPC .......... *C12N 15/52* (2013.01); *C12Q 1/6876* (2013.01); *C12Q 2600/112* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2012/0027786 A1 | 2/2012 | Gupta et al. |
| 2013/0007913 A1 | 1/2013 | Medford et al. |
| 2013/0202532 A1 | 8/2013 | Benenson et al. |

FOREIGN PATENT DOCUMENTS

WO  WO 2015/185692 A1  12/2015

OTHER PUBLICATIONS

Hansen et al. PNAS vol. 111, pp. 15705-15710 (Year: 2014).*
Gam et al. Nature Communications 9:2430, pp. 1-12 (Year: 2018).*
Gordley et al. PNAS vol. 113 pp. 13528-13533 (Year: 2016).*
Hsing et al. Journal of Bacteriology vol. 179, p. 3729-3735 (Year: 1997).*
Yeh et al. ACS Chem, Biol. 14: 959-965 (Year: 2019).*
Chavez et al., Highly efficient Cas9-mediated transcriptional programming. Nat. Methods. 2015;12:326-328.
Duportet et al., A platform for rapid prototyping of synthetic gene networks in mammalian cells. Nucleic Acids Res. 2014;42:13440-13451.
Sedlmayer et al., Synthetic gene circuits for the detection, elimination and prevention of disease. Nat Biomed Engin. Jun. 11, 2018;2(6):399-415. doi: 10.1038/S41551-018-0215-0.
Wagner, Engineering a regulatory framework for synthetic self-amplifying RNA circuits. Dissertation. Boston University. 2017. 133 pages.
Xie et al., Multi-input RNAi-based logic circuit for identification of specific cancer cells. Science. 2011; 333:1307-1311.

* cited by examiner

*Primary Examiner* — Brian Whiteman
(74) *Attorney, Agent, or Firm* — Wolf, Greenfield & Sacks, P.C.

(57) ABSTRACT

Provided herein are genetic circuits and cell state classifiers for detecting the microRNA profile of a cell. The cell state classifiers of the present disclosure utilize phosphorylation state of a transcription factor to control classifier output. Kinases and phosphatase pairs that function in phosphorylating or dephosphorylating the transcription factor are integrated into the circuit, their expression tuned by the presence of microRNAs of interest (e.g., in a cell). The genetic circuits and cell state classifiers may be used in various applications (e.g., therapeutic or diagnostic applications).

18 Claims, 4 Drawing Sheets
Specification includes a Sequence Listing.

PHOSPHORYLATION-BASED miRNA SENSOR

RELATED APPLICATIONS

This application is a continuation of U.S. patent application Ser. No. 16/528,772, filed Aug. 1, 2019, which claims the benefit of the filing date under 35 U.S.C. § 119 of U.S. Provisional Application Ser. No. 62/713,160, filed Aug. 1, 2018, the entire contents of each of which are incorporated by reference herein.

GOVERNMENT SUPPORT

This invention was made with government support under GM098792 awarded by the National Institutes of Health. The Government has certain rights in the invention.

REFERENCE TO AN ELECTRONIC SEQUENCE LISTING

The contents of the electronic sequence listing (M065670450US02-SUBSEQ-JRV.xml; Size: 43,953 bytes; and Date of Creation: Nov. 10, 2022) is herein incorporated by reference in its entirety.

BACKGROUND

The microRNA (miRNA) profile of each cell type varies and may serve as cellular input for a genetic circuit designed to detect cell types of interest. The genetic circuit may also be designed such that an output molecule is expressed when a matching miRNA profile is detected. The genetic circuit can rely on the activation and repression of various components. Balancing the activation and repression strength such that the genetic circuit accurately responds to the microRNA input remains challenging.

SUMMARY

Provided herein are genetic circuits and cell state classifiers that utilize the phosphorylation state of a transcription factor to control classifier output. Kinases and phosphatase pairs that function in phosphorylating or dephosphorylating the transcription factor are integrated into the circuit, their expression tuned by the presence of microRNAs of interest (e.g., in a cell). The transcription factor undergoes a conformational change upon phosphorylation or dephosphorylation, allowing or abrogating its DNA-binding ability, thus controlling the expression of an output molecule. With this design, the activation/repression strength are easily tunable and the performance of the cell state classifier is enhanced.

Accordingly, some aspects of the present disclosure provide cell state classifiers, containing: (i) a first sensor circuit containing a constitutive promoter operably linked to a nucleotide sequence encoding an activator, and a constitutive promoter operably linked to a nucleotide sequence encoding a kinase that phosphorylates the activator and produces a phosphorylated activator, and one or more target sites for a first microRNA; (ii) a second sensor circuit containing a constitutive promoter operably linked to a nucleotide sequence encoding a phosphatase that de-phosphorylates the phosphorylated activator, and one or more target sites for a second microRNA; and (iii) a signal circuit containing an activatable promoter that is activated by the phosphorylated activator, operably linked to a nucleotide sequence encoding an output molecule, and one or more target sites for the first microRNA.

In some embodiments, the constitutive promoter of (i) and the constitutive promoter of (ii) are the same. In some embodiments, the constitutive promoter of (i) and the constitutive promoter of (ii) are different.

In some embodiments, the kinase, the phosphatase, and/or the activator are members of a bacterial two-component signaling system. In some embodiments, bacterial two-component system contains a histidine kinase contains an amino acid sequence motif of HEXXN, HEXXT, or HDXXXP, wherein X is any amino acid, such as any naturally occurring amino acid, and a response regulator.

In some embodiments, the kinase is a variant of the histidine kinase an amino acid substitution in the N, T, or P of the HEXXN, HEXXT or HDXXXP motif. In some embodiments, the kinase contains an alanine substitution in the N, T, or P of the HEXXN, HEXXT, or HDXXXP motif.

In some embodiments, the phosphatase is a histidine kinase variant containing an amino acid substitution in the E or D of the HEXXN, HEXXT, or HDXXXP motif. In some embodiments, the phosphatase contains an alanine substitution in the E or D of the HEXXN, HEXXT, or HDXXXP motif.

In some embodiments, the histidine kinase is selected from the group consisting of: EnvZ, NarX, and PhoR. In some embodiments, the histidine kinase is EnvZ. In some embodiments, the histidine kinase contains the amino acid sequence of SEQ ID NO: 1. In some embodiments, the phosphatase contains an amino acid substitution corresponding to a D244A substitution in SEQ ID NO: 1. In some embodiments, the phosphatase contains the amino acid sequence of SEQ ID NO:2. In some embodiments, the kinase contains an amino acid substitution corresponding to a T247A substitution in SEQ ID NO: 1. In some embodiments, the kinase contains the amino acid sequence of SEQ ID NO: 3. In some embodiments, the phosphatase contains a dimerization and histidine phosphorylation (DHp) domain of EnvZ. In some embodiments, the phosphatase contains the amino acid sequence of SEQ ID NO: 4. In some embodiments, the kinase contains two DHp domains fused to a cytoplasmic domain of EnvZ. In some embodiments, the kinase contains the amino acid sequence of SEQ ID NO: 5.

In some embodiments, the activator contains the response regulator of the bacterial two-component system. In some embodiments, the activator contains the response regulator of the bacterial two-component system fused to an activator domain. In some embodiments, the activation domain is selected from the group consisting of: VP16, VP64, p65, and VPR. In some embodiments, the response regulator is selected from the group consisting of: OmpR, NarL, NtrC, and PhoB. In some embodiments, the response regulator is OmpR.

In some embodiments, the activatable promoter contains one or more response elements that binds to the activator. In some embodiments, the response element contains one or more operators of the activator. In some embodiments, the activatable promoter further contains a minimal promoter fused to the one or more response elements.

In some embodiments, the one or more target sites for the first microRNA is located upstream and/or downstream of the nucleotide sequence encoding the activator and the nucleotide sequence encoding the kinase in the first sensor circuit. In some embodiments, 4 target sites for the first microRNA are located upstream and/or downstream of the nucleotide sequence encoding the activator and the nucleotide sequence encoding the kinase in the first sensor circuit.

In some embodiments, the one or more target sites for the first microRNA is located upstream and/or downstream of the nucleotide sequence encoding the output molecule in the signal circuit. In some embodiments, 4 target sites for the first microRNA are located upstream and/or downstream of the nucleotide sequence encoding the output molecule in the signal circuit.

In some embodiments, the one or more target sites for the second microRNA is located upstream and/or downstream of the nucleotide sequence encoding the phosphatase in the second sensor circuit. In some embodiments, 4 target sites for the second microRNA are located upstream and/or downstream of the nucleotide sequence encoding the phosphatase in the second sensor circuit.

In some embodiments, the output molecule is a detectable molecule. In some embodiments, the output molecule is a therapeutic molecule.

Cells containing the cell state classifies described herein are provided. In some embodiments, the cell is a prokaryotic cell. In some embodiments, the cell is a bacterial cell. In some embodiments, the cell is a eukaryotic cell. In some embodiments, the eukaryotic cell is a plant cell, an insect cell, or a mammalian cell. In some embodiments, the mammalian cell is a human cell. In some embodiments, the cell is a diseased cell. In some embodiments, the cell is a cancer cell.

In some embodiments, the cell does not express the first microRNA. In some embodiments, the cell expresses the second microRNA. In some embodiments, the cell expresses the first microRNA and does not express the second microRNA. In some embodiments, the cell expresses the first microRNA and expresses the second microRNA. In some embodiments, the cell does not express the first microRNA and does not express the second microRNA.

Other aspects of the present disclosure provide methods comprising maintaining the cells containing the cell state classifiers described herein. In some embodiments, the method further comprises detecting the output molecule. In some embodiments, the method further comprises classifying the cell.

Other aspects of the present disclosure provide methods comprising delivering the cell state classifier described herein to a cell and detecting an output molecule.

Methods of treating or a disease or disorder are also provided, such methods comprising delivering the cell state classifier described herein to a cell, wherein the output molecule is a therapeutic molecule that is effective for treating the disease or disorder. In some embodiments, the method comprises administering an effective amount of a composition containing the cell state classifier described herein to a subject in need thereof, wherein the output molecule is a therapeutic molecule that is effective for treating the disease or disorder. In some embodiments, the composition further comprises a pharmaceutically acceptable carrier. In some embodiments, the cell is a diseased cell. In some embodiments, the cell is a cancer cell.

Methods of diagnosing a disease or disorder are provided, such methods comprising delivering the cell state classifier described herein to a cell. In some embodiments, the method comprises administering an effective amount of a composition containing the cell state classifier described herein to a subject in need thereof, and detecting the output molecule. In some embodiments, the composition further comprises a pharmaceutically acceptable carrier. In some embodiments, the cell is a diseased cell. In some embodiments, the cell is a cancer cell. In some embodiments, the method further comprise detecting the output molecule. In some embodiments, the expression of the output molecule indicates the disease or disorder. In some embodiments, the lack of expression of the output molecule indicates the disease or disorder.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

The accompanying drawings are not intended to be drawn to scale. For purposes of clarity, not every component may be labeled in every drawing.

DETAILED DESCRIPTION OF CERTAIN EMBODIMENTS

Figure 1:
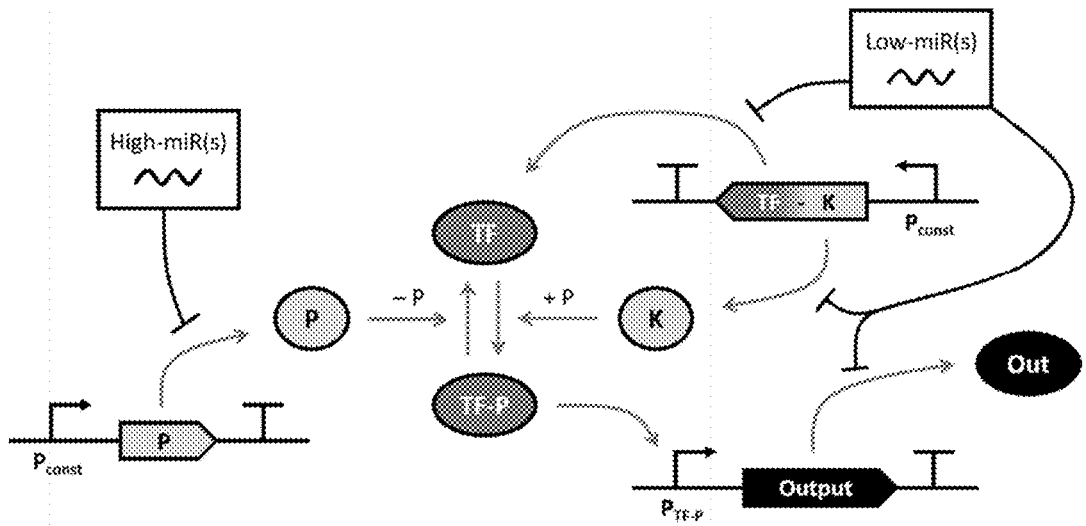
FIG. 1: Circuit Schematic. P: phosphatase, K: kinase, TF: unphosphorylated transcription factor (inactive), TF-P: phosphorylated transcription factor (active), $P_{const}$: a constitutive promoter, $P_{TF-P}$: TF-P activated promoter.

Described herein are cell state classifiers that can detect the microRNA profile of a cell and classify the cell accordingly. The cell state classifiers described herein utilize the phosphorylation state of a transcription factor to control classifier output. The transcription factor undergoes a conformational change upon phosphorylation, allowing or abrogating its DNA-binding ability. Kinases and phosphatase pairs that function in phosphorylating or dephosphorylating the transcription factor are integrated into the circuit, their expression level tuned by the presence of microRNAs of interest (e.g., in a cell). In some embodiments, the transcription factor, the kinase, and the phosphatase are derived from members of bacterial two-component signaling system. The repression and activation strength of the different components in the cell state classifier described herein easy tuned and balanced, allowing the cell state classifier to accurately sense the microRNA profile of a cell and to classify the cell accordingly.

A "cell state classifier," as used herein, refers to a system with multiple genetic circuits integrated together by transcriptional or translational control, which is able to sense a microRNA profile (e.g., one or more microRNAs) in a cell and produce an output molecule (e.g., a detectable molecule or a therapeutic molecule) accordingly. A "microRNA profile," as used herein, refers to the expression levels of one or more microRNAs in a cell or a cell type. The microRNA profile may contain expression levels of microRNAs that have no expression or lower expression (e.g., at least 30% lower), and/or expression levels of microRNAs that express or have higher expression (e.g., at least 30% higher) in a cell or a cell type, compared to another cell or a different cell type, respectively. MicroRNAs that have no expression or lower expression is referred to herein as "microRNA-low" or "miR-low," while microRNAs that express or have high expression is referred to herein as "microRNA-high" or "miR-high."

In part, the cell state classifier of the present disclosure is designed to detect miRNA by incorporating target sites of the miRNA to be detected into different genetic circuits (e.g., sensor circuit and/or signal circuit). Expression of the microRNA leads to the degradation of mRNAs encoding the molecules that are produced by these circuits (e.g., activators, repressors, or output molecules), thus leading to different signal output by the cell state classifier, which may be detected and used for classifying the cell.

Sensing of multiple inputs (e.g., microRNAs) simultaneously is enabled by coupling their detection to different portions of the genetic circuit such that the output molecule is produced only when the correct input profile of miRNAs is detected. The cell state classifier may be used in various applications. In some embodiments, the cell state classifier described herein is used for the detection of a diseased cell (e.g., a cancer cell). In some embodiments, detection of the diseased cell (e.g., the cancer cell) is achieved via the expression of a detectable output molecule (e.g., a fluorescent protein) upon detection of a matching microRNA profile. As such, the cell state classifier of the present disclosure may be used for diagnosing a disease (e.g., cancer). In some embodiments, detection of the diseased cell (e.g., a cancer cell) is coupled with the expression of a therapeutic molecule for treating a disease (e.g., cancer). Further, to evaluate the performance of the cell state classifiers described herein, a large combinatorial library of circuit variants are generated and the performance of each circuit variant may be evaluated in living cell assays.

Components of the Cell State Classifier

The cell state classifier described herein comprises various genetic circuits (also termed "circuits") that perform different functions. A "genetic circuit" is a functional unit of the cell state classifier. The genetic circuits of the present disclosure may function in sensing the microRNA profile, producing output molecules, producing control signal, or regulating the signals sensed or produced by the cell state classifier.

In some embodiments, the cell state classifier comprises one or more (e.g., 1, 2, 3, 4, 5, 6, 7, 8, 9, 10, or more) sensor circuits. A "sensor circuit" is a genetic circuit that detects the microRNA profile of the cell. Different types of sensor circuits are used in the cell state classifier for detecting microRNA-high and microRNA-low. Sensor circuits comprise microRNA target sites for the microRNAs to be detected.

The cell state classifier described herein comprises a first sensor circuit that detects a first microRNAs that does not express or expresses at a low (e.g., undetectable) level in a cell. Such first microRNA is referred to as "microRNA-low" or "miR-low" herein. The first sensor circuit is also referred to interchangeably herein as the "microRNA-low sensor" or "miR-low sensor." As described herein, the first sensor circuit comprises one or more (e.g., 1, 2, 3, 4, 5, 6, 7, 8, 9, 10, or more) target sites of the first microRNA (microRNA-low) to be detected. In some embodiments, one first sensor circuit is used for the detection of one or multiple (e.g., 2, 3, 4, 5, 6, 7, 8, 9, 10, or more) microRNA-low.

The first sensor circuit further comprises a constitutive promoter operably linked to a nucleotide sequence encoding an activator and a constitutive promoter operably linked to a nucleotide sequence encoding a kinase that phosphorylates the activator. Phosphorylation of the activator by the kinase produces a phosphorylated activator. A "kinase" is an enzyme that catalyzes the transfer of a phosphate group from ATP to a specified molecule (e.g., a protein), and the process is known as "phosphorylation." During phosphorylation, the substrate (e.g., a protein) gains a phosphate group and the high-energy ATP molecule donates a phosphate group, producing a phosphorylated substrate and ADP. Kinases are part of the larger family of phosphotransferases. The phosphorylation state of a molecule, e.g., protein, lipid, or carbohydrate, can affect its activity, reactivity, and its ability to bind other molecules. Therefore, kinases are critical in metabolism, cell signaling, protein regulation, cellular transport, secretory processes, and many other cellular pathways. For kinases that phosphorylate proteins, the phosphate group may be transferred to a serine, a threonine, tyrosine, or a histidine residue in the protein. Non-limiting examples of kinases include serine kinases, threonine kinases, tyrosine kinase, and histidine kinases. In accordance with the present disclosure, the kinase of the first sensor circuit phosphorylates the activator, producing a phosphorylated activator, which causes a conformational change in the activator, allowing it to bind to its target DNA sequence, e.g., promoter.

In some embodiments, the nucleotide sequences encoding kinase and the activator is placed under the control of one constitutive promoter. As such, the activator and the kinase is transcribed into one polycistronic mRNA containing two different coding sequences (or open reading frames (ORF)). In some embodiments, the activator and the kinase are translated from the polycistronic mRNA into a fusion protein, provided that the kinase is able to phosphorylate the activator when it is fused to the activator. Alternatively, in some embodiments, translation of the activator and the kinase can initiate and proceed independently on the two coding sequences, producing the activator and the kinase as individual proteins, e.g., by placing an internal ribosomal entry site (IRES) between the nucleotide sequence encoding the activator and the nucleotide sequence encoding the kinase. In some embodiments, the nucleotide sequence encoding the activator and the nucleotide sequence encoding the kinase are each placed under control of a constitutive promoter, and is transcribed and translated independently into individual proteins. In this instance, the two constitutive promoters may be different or the same.

In some embodiments, in the first sensor circuit, the one or more (e.g., 1, 2, 3, 4, 5, 6, 7, 8, 9, 10, or more) target sites for the first microRNA are inserted into non-coding regions of the circuit. For example, such non-coding region may be upstream and/or downstream of the nucleotide sequence encoding the activator and/or the kinase, or between the nucleotide sequence encoding the activator and the nucleotide sequence encoding the kinase. In some embodiments, four target sites for the first microRNA are used at each insertion site.

The cell state classifier described herein comprises a second sensor circuit that detects a second microRNA that expresses (e.g., expression level is detectable or high) in a cell. Such second microRNA are referred to as "microRNA-high" or "miR-high" herein. The second sensor circuit is also referred to interchangeably herein as the "microRNA-high sensor" or "miR-high sensor." The second sensor circuit comprises one or more (e.g., 1, 2, 3, 4, 5, 6, 7, 8, 9, 10, or more) target sites of the second microRNA (microRNA-high), and a constitutive promoter operably linked to a nucleotide sequence encoding a phosphatase that dephosphorylates the phosphorylated activator. A "phosphatase" is an enzyme that uses water to cleave a phosphoric acid monoester into a phosphate ion and an alcohol, a process known as "dephosphorylation." Phosphatase enzymes are essential to many biological functions, because phosphorylation (e.g. by protein kinases) and dephosphorylation (by phosphatases) serve diverse roles in cellular regulation and signaling. Phosphatases that catalyzes the removal of a phosphate group from an amino acid residue in a protein is referred to as a "protein phosphatase."

In some embodiments, the one or more (e.g., 1, 2, 3, 4, 5, 6, 7, 8, 9, 10, or more) target sites for the second microRNA are placed in a non-coding region of the second sensor circuit, e.g., upstream and/or downstream of the nucleotide sequence encoding the phosphatase. In some embodiments, the target sites for the second microRNA are upstream of the nucleotide sequence encoding the phosphatase. In some embodiments, the target sites for the second microRNA are downstream of the nucleotide sequence encoding the phosphatase. In some embodiments, the target sites for the second microRNA are downstream and upstream of the nucleotide sequence encoding the phosphatase. In some embodiments, four target sites for the second microRNA are used at each insertion site.

In some embodiments, the constitutive promoters in the first and second sensor circuits are the same. In some embodiments, the constitutive promoters in the first and second sensor circuits are different.

The cell state classifier described herein further comprises a signal circuit. A "signal circuit," as used herein, refers to a genetic circuit that responds to the sensor circuits and in turn produces an output molecule. The signal circuit of the present disclosure comprises one or more (e.g., 1, 2, 3, 4, 5, 6, 7, 8, 9, 10, or more) target sites for the first microRNA (microRNA-low), and an activatable promoter operably linked to a nucleotide sequence encoding an output molecule. In some embodiments, in the signal circuit, the one or more (e.g., 1, 2, 3, 4, 5, 6, 7, 8, 9, 10, or more) target sites for the first microRNA are placed in a non-coding region of the signal circuit, e.g., upstream and/or downstream of the nucleotide sequence encoding the output molecule. In some embodiments, the target sites for the first microRNA are downstream of the nucleotide sequence encoding the output molecule. In some embodiments, the target sites for the first microRNA are upstream of the nucleotide sequence encoding the output molecule. In some embodiments, the target sites for the first microRNA are downstream and upstream of the nucleotide sequence encoding the output molecule. In some embodiments, 4 target sites for the first microRNA are used at each insertion site.

An "activatable promoter" is a promoter that can be activated (e.g., by an activator) to drive the expression of the nucleotide sequence that it is operably linked to. In the signal circuit, the activatable promoter is activated by the phosphorylated activator produced by the first sensor circuit. When a matching microRNA profile is present, the activatable promoter is activated and the output molecule is produced. In some embodiments, the output molecule is a detectable molecule. As such, detection of the output molecule is an indication that a matching miRNA profiling is present in a cell.

The cell state classifier of the present disclosure utilizes the phosphorylation state of the activator to control the expression of the output molecule. In some embodiments, the kinase, the phosphatase, and/or the activator are members of a bacterial two-component system. A "bacterial two-component system" is a stimulus-response coupling mechanism that allows bacterial cells to sense and respond to changes in many different environmental conditions. Two-component systems typically consist of a membrane-bound histidine kinase (HK) that senses a specific environmental stimulus and a corresponding response regulator (RR) that mediates the cellular response, mostly transcriptional regulation (e.g., activation or repression) of target genes. The histidine kinase and its cognate RR typically functions orthogonally, and are referred to hear in as a "HK-RR pair." In some embodiments, the kinase, the phosphatase, and the activator of the cell state classifier described herein are derived from the same HK-RR pair.

Without wishing to be bound by scientific theory, each HK-RR pair accomplishes signal transduction through the phosphorylation of the response regulator by the histidine kinase. Histidine kinases are typically homodimeric transmembrane proteins that contain a dimerization and histidine phosphorylation domain (DHp).

A "response regulator (RR)" is a protein that mediates a cell's response to changes in its environment as part of a two-component regulatory system. Response regulators are coupled to specific histidine kinases which serve as sensors of environmental changes. Many response regulators are transcriptional factors, and their binding to DNA is controlled by this conformational change. Response regulators typically consist of a receiver domain and one or more effector domains, although in some cases they possess only a receiver domain and exert their effects through protein-protein interactions.

In the absence of signal input, HKs act as a phosphatase on their cognate RR. Upon extracellular signal induction, the HK will auto-phosphorylate a conserved histidine residue in the dimerization and histidine phosphorylation (DHp) domain of itself. The phosphate group is then rapidly transferred to the HK's cognate RR protein on a conserved aspartate residue in the receiver domain of the protein. This phosphate group causes a conformational change in the RR that allows it to bind a target DNA sequence (e.g., a promoter) and activate/repress the expression of a gene.

A large number of bacterial two-component systems (e.g., HK and RR pairs) are known and may be used in accordance with the present disclosure. Information regarding bacterial two-component systems are available in the art, e.g., in public databases such as p2cs.org. Non-limiting examples of *E. coli* two-component systems include the EnvZ-OmpR system, the NarX-NarL system, the NtrB-NtrC system, and the PhoR-PhoB system.

In some embodiments, the histidine kinase in the bacterial two-components system comprises a conserved amino acid sequence motif of HEXXN, HEXXT, or HDXXXP, wherein X is any amino acid, such as any naturally occurring amino acid. The histidine (H) in the conserved motif can undergo autophosphorylation upon a signal input and became a phosphohistidine ($H_p$). Non-limiting examples of histidine kinases from bacterial two-component systems that may be used in accordance with the present disclosure include: Osmolarity sensor protein (EnvZ), Nitrate/nitrite sensor protein (NarX), Nitrogen regulation protein NR(II) (NtrB), and Phosphate regulon sensor protein PhoR (PhoR). In some embodiments, the histidine kinase is EnvZ, which comprises a conserved HEXXT motif. The histidine kinases may be from any bacterial species that genetically encodes them, e.g., *Escherichia coli*. Gene and protein sequences of the histidine kinases described herein are available in the art, e.g., in public databases such as the GENBANK®.

In some embodiments, the kinase encoded by the sensor circuit of the cell state classifier is a variant of the histidine kinase in the bacterial two-component system. As demonstrated herein, the kinase and phosphatase activities of a histidine kinase from a bacterial two-component system are separated by modifying its amino acid sequence. Typically, to generate a kinase, the asparagine (N), threonine (T), or proline (P) of the conserved motif is substituted by a different amino acid, e.g., replaced by alanine (A). To generate a phosphatase, the glutamic acid (E) or aspartic acid (D) of the conserved motif is substituted by a different amino acid, e.g., replaced by A.

Accordingly, in some embodiments, the kinase of the first sensor circuit comprises an amino acid substitution in N, T, or P of the HEXXN, HEXXT, or HDXXXP motifs, respectively. In some embodiments, the kinase of the first sensor circuit comprises an alanine (A) substitution in the N, T, or P of the HEXXN, HEXXT, or HDXXXP motif, respectively. As such, in some embodiments, the kinase of the first sensor circuit comprises a motif of the amino acid sequence of: HEXXA or HDXXXA, wherein X is any amino acid, such as any naturally occurring amino acid.

In some embodiments, the phosphatase of the second sensor circuit comprises an amino acid substitution in E or D of the HEXXN, HEXXT, or HDXXXP motif, respectively. In some embodiments, the phosphatase of the second sensor circuit comprises an alanine substitution in E or D position of the HEXXN, HEXXT, or HDXXXP motif, respectively. As such, in some embodiments, the phosphatase of the second sensor circuit comprises a motif of the amino acid sequence of HAXXN, HAXXT, or HAXXXP, wherein X is any amino acid, such as any naturally occurring amino acid.

In some embodiments, the histidine kinase is EnvZ (e.g., *E. coli* EnvZ, SEQ ID NO: 1) and the kinase and phosphatase of the cell state classifier described herein are variants of EnvZ. In some embodiments, the kinase encoded by the first sensor circuit is an EnvZ variant comprising an amino acid substitution corresponding to a T247A substitution in SEQ ID NO: 1. In some embodiments, the kinase encoded by the first sensor circuit comprises the amino acid sequence of SEQ ID NO: 3. In some embodiments, the kinase encoded by the first sensor circuit comprises an amino acid sequence that is at least 80%, at least 85%, at least 90%, at least 95%, or at least 99% identical to the amino acid sequence of SEQ ID NO: 3, and comprises an amino acid substitution corresponding to a T247A substitution in SEQ ID NO: 1. In some embodiments, the kinase encoded by the first sensor circuit comprises an amino acid sequence that is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 3, and comprises an amino acid substitution corresponding to a T247A substitution in SEQ ID NO: 1. In some embodiments, the kinase encoded by the first sensor circuit consists of the amino acid sequence of SEQ ID NO: 3.

In some embodiments, the kinase encoded by the first sensor circuit comprises two DHp domains of EnvZ fused to a cytoplasmic domain of EnvZ. In some embodiments, the kinase encoded by the first sensor circuit comprises the amino acid sequence of SEQ ID NO: 5. In some embodiments, the kinase encoded by the first sensor circuit comprises an amino acid sequence that is at least 80%, at least 85%, at least 90%, at least 95%, or at least 99% identical to the amino acid sequence of SEQ ID NO: 5. In some embodiments, the kinase encoded by the first sensor circuit may comprise an amino acid sequence that is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 5. In some embodiments, the kinase of the first sensor circuit consists of the amino acid sequence of SEQ ID NO: 5.

In some embodiments, the phosphatase encoded by the second sensor circuit is an EnvZ variant comprising an amino acid substitution corresponding to a D244A substitution in SEQ ID NO: 1. In some embodiments, the phosphatase encoded by the second sensor circuit comprises the amino acid sequence of SEQ ID NO: 2. In some embodiments, the phosphatase encoded by the second sensor circuit comprises an amino acid sequence that is at least 80%, at least 85%, at least 90%, at least 95%, or at least 99% identical to the amino acid sequence of SEQ ID NO: 2, and comprises an amino acid substitution corresponding to a D244A substitution in SEQ ID NO: 1. In some embodiments, the phosphatase encoded by the second sensor circuit comprises an amino acid sequence that is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 2, and comprises an amino acid substitution corresponding to a D244A substitution in SEQ ID NO: 1. In some embodiments, the phosphatase encoded by the second sensor circuit consists of the amino acid sequence of SEQ ID NO: 2.

In some embodiments, the phosphatase encoded by the second sensor circuit comprises a dimerization and histidine phosphorylation (DHp) domain of EnvZ. In some embodiments, the phosphatase encoded by the second sensor circuit comprises the amino acid sequence of SEQ ID NO: 4. In some embodiments, the phosphatase encoded by the second sensor circuit comprises an amino acid sequence that is at least 80%, at least 85%, at least 90%, at least 95%, or at least 99% identical to the amino acid sequence of SEQ ID NO: 4. In some embodiments, the phosphatase encoded by the second sensor circuit comprises an amino acid sequence that is 80%, 81%, 82%, 83%, 84%, 85%, 86%, 87%, 88%, 89%, 90%, 91%, 92%, 93%, 94%, 95%, 96%, 97%, 98%, or 99% identical to the amino acid sequence of SEQ ID NO: 4. In some embodiments, the phosphatase of the second sensor circuit consists of the amino acid sequence of SEQ ID NO: 4.

Wild Type EnvZ amino acid sequence
(SEQ ID NO: 1)
MRRLRFSPRSSFARTLLLIVTLLFASLVTTYLVVLNFAILPSLQQFNKV

LAYEVRMLMTDKLQLEDGTQLVVPPAFRREIYRELGISLYSNEAAEEAG

LRWAQHYEFLSHQMAQQLGGPTEVRVEVNKSSPVVWLKTWLSPNIWVRV

PLTEIHQGDFSPLFRYTLAIMLLAIGGAWLFIRIQNRPLVDLEHAALQV

GKGIIPPPLREYGASEVRSVTRAFNHMAAGVKQLADDRTLLMAGVSHDL

RTPLTRIRLATEMMSEQDGYLAESINKDIEECNAIIEQFIDYLRTGQEM

PMEMADLNAVLGEVIAAESGYEREIETALYPGSIEVKMHPLSIKRAVAN

MVVNAARYGNGWIKVSSGTEPNRAWFQVEDDGPGIAPEQRKHLFQPFVR

GDSARTISGTGLGLAIVQRIVDNHNGMLELGTSERGGLSIRAWLPVPVT

RAQGTTKEG

EnvZ D244A (Phosphatase) amino acid sequence
(SEQ ID NO: 2)
MRRLRFSPRSSFARTLLLIVTLLFASLVTTYLVVLNFAILPSLQQFNKV

LAYEVRMLMTDKLQLEDGTQLVVPPAFRREIYRELGISLYSNEAAEEAG

LRWAQHYEFLSHQMAQQLGGPTEVRVEVNKSSPVVWLKTWLSPNIWVRV

PLTEIHQGDFSPLFRYTLAIMLLAIGGAWLFIRIQNRPLVDLEHAALQV

GKGIIPPPLREYGASEVRSVTRAFNHMAAGVKQLADDRTLLMAGVSHAL

RTPLTRIRLATEMMSEQDGYLAESINKDIEECNAIIEQFIDYLRTGQEM

PMEMADLNAVLGEVIAAESGYEREIETALYPGSIEVKMHPLSIKRAVAN

MVVNAARYGNGWIKVSSGTEPNRAWFQVEDDGPGIAPEQRKHLFQPFVR

GDSARTISGTGLGLAIVQRIVDNHNGMLELGTSERGGLSIRAWLPVPVT

RAQGTTKEG

EnvZ T247A (Kinase) amino acid sequence
(SEQ ID NO: 3)
MRRLRFSPRSSFARTLLLIVTLLFASLVTTYLVVLNFAILPSLQQFNKV

LAYEVRMLMTDKLQLEDGTQLVVPPAFRREIYRELGISLYSNEAAEEAG

LRWAQHYEFLSHQMAQQLGGPTEVRVEVNKSSPVVWLKTWLSPNIWVRV

PLTEIHQGDFSPLFRYTLAIMLLAIGGAWLFIRIQNRPLVDLEHAALQV

GKGIIPPPLREYGASEVRSVTRAFNHMAAGVKQLADDRTLLMAGVSHDL

RAPLTRIRLATEMMSEQDGYLAESINKDIEECNAIIEQFIDYLRTGQEM

PMEMADLNAVLGEVIAAESGYEREIETALYPGSIEVKMHPLSIKRAVAN

MVVNAARYGNGWIKVSSGTEPNRAWFQVEDDGPGIAPEQRKHLFQPFVR

GDSARTISGTGLGLAIVQRIVDNHNGMLELGTSERGGLSIRAWLPVPVT

RAQGTTKEG

EnvZ DHp (Phosphatase) amino acid sequence
(SEQ ID NO: 4)
MAAGVKQLADDRTLLMAGVSHDLRAPLTRIRLATEMMSEQDGYLAESIN

KDIEECNAIIEQFIDYLR

EnvZ DHp-DHp-CA (Kinase) amino acid sequence
(SEQ ID NO: 5)
MAAGVKQLADDRTLLMAGVSHDLRTPLTRIRLATEMMSEQDGYLAESIN

KDIEECNAIIEQFIDYLRGGSIGGSIMAAGVKQLADDRTLLMAGVSHDL

RTPLTRIRLATEMMSEQDGYLAESINKDIEECNAIIEQFIDYLRTGQEM

PMEMADLNAVLGEVIAAESGYEREIETALYPGSIEVKMHPLSIKRAVAN

MVVNAARYGNGWIKVSSGTEPNRAWFQVEDDGPGIAPEQRKHLFQPFVR

GDSARTISGTGLGLAIVQRIVDNHNGMLELGTSERGGLSIRAWLPVPVT

RAQGTTKEG

An "amino acid substitution" without the reference to a specific amino acid, may include any amino acid other than the wild type residue normally found at that position. Such substitutions may be replacement with non-polar (hydrophobic) amino acids, such as glycine, alanine, valine, leucine, isoleucine, methionine, phenylalanine, tryptophan, and proline. Substitutions may be replacement with polar (hydrophilic) amino acids such as serine, threonine, cysteine, tyrosine, asparagine, and glutamine. Substitutions may be replacement with electrically charged amino acids, e.g., negatively electrically charged amino acids such as aspartic acid and glutamic acid and positively electrically charged amino acids such as lysine, arginine, and histidine.

The substitution mutations described herein will typically be replacement with a different naturally occurring amino acid residue, but in some cases non-naturally occurring amino acid residues may also be used for the substitution. Non-natural amino acids, as the term is used herein, are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, di-amino acids, D-amino acids, and N-methyl amino acids.

The term "identity" refers to the overall relatedness between biological molecule, for example, polypeptide molecules. Calculation of the percent identity of two polypeptide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The amino acids at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. Exemplary computer software to determine homology between two sequences include, but are not limited to BLASTP, CLUSTAL, and MAFFT.

In some embodiments, the activator encoded by the signal circuit comprises a response regulator (RR) of the bacterial two-component system. In some embodiments, the activator comprises the RR fused to and activation domain. An "activation domain," as used herein, refers to a protein or protein domain that in conjunction with a DNA binding domain (e.g., the RR of the present disclosure), can activate transcription from a promoter. Any activation domains known in the art may be used in accordance with the present disclosure. Non-limiting examples of activation domains include: VP16, VP64, p65, and VPR and exemplary sequences are provided in Table 1. "Fuse" means to connect two different protein partners, e.g., via an amide bond, thus to form a fusion protein. In some embodiments, the RR is fused at the N terminus of the activation domain. In some embodiments, the RR is fused at the C-terminus of the activation domain.

TABLE 1

Non-limiting, Exemplary Activation Domains

| Activation Domain | Amino Acid Sequence |
|---|---|
| VP16 | APPTDVSLGDELHLDGEDVAMAHADALDDFDLDMLGDGD SPGPGFTPHDSAPYGALDMADFEFEQMFTDALGIDEYGG (SEQ ID NO: 6) |
| VP64 | EASGSGRADALDDFDLDMLGSDALDDFDLDMLGSDALDD FDLDMLGSDALDDFDLDML INSR(SEQ ID NO: 7) |
| P65 | SQYLPDTDDRHRIEEKRKRTYETFKSIMKKSPFSGPTDP RPPPRRIAVPSRSSASVPKPAPQPYPFTSSLSTINYDEF PTMVFPSGQISQASALAPAPPQVLPQAPAPAPAPAMVSA LAQAPAPVPVLAPGPPQAVAPPAPKPTQAGEGTLSEALL QLQFDDEDLGALLGNSTDPAVFTDLASVDNSEFQQLLNQ GIPVAPHTTEPMLMEYPEAITRLVTGAQRPPDPAPAPLG APGLPNGLLSGDEDFSSIADMDFSALL (SEQ ID NO: 8) |
| VPR | RADALDDFDLDMLGSDALDDFDLDMLGSDALDDFDLDML GSDALDDFDLDMLINSRSSGSPKKKRKVGSQYLPDTDDR HRIEEKRKRTYETFKSIMKKSPFSGPTDPRPPPRRIAVP SRSSASVPKPAPQPYPFTSSLSTINYDEFPTMVFPSGQI SQASALAPAPPQVLPQAPAPAPAPAMVSALAQAPAPVPV LAPGPPQAVAPPAPKPTQAGEGTLSEALLQLQFDDEDLG ALLGNSTDPAVFTDLASVDNSEFQQLLNQGIPVAPHTTE PMLMEYPEAITRLVTGAQRPPDPAPAPLGAPGLPNGLLS GDEDFSSIADMDFSALLGSGSGSRDSREGMFLPKPEAGS AISDVFEGREVCQPKRIRPFHPPGSPWANRPLPASLAPT PTGPVHEPVGSLTPAPVPQPLDPAPAVTPEASHLLEDPD EETSQAVKALREMADTVIPQKEEAAICGQMDLSHPPPRG HLDELTTTLESMTEDLNLDSPLTPELNEILDTFLNDECL LHAMHISTGLSIFDTSLF (SEQ ID NO: 9) |

Any RRs that are known in the art may be used in the activator of the present disclosure, including, without limitation: OmpR, NarL, NtrC, and PhoB and exemplary sequences are provided in Table 2. It is to be understood that the RRs need to be used in conjunction with its cognate histidine kinase and phosphatase, since most bacterial two-component systems are orthogonal. For example, when the kinase and the phosphatase in the cell state classifier are derived from EnvZ, OmpR is used in the activator, e.g., to be used with an activation domain such as VP16, VP64, p65, or VPR, to form the activator encoded by the signal circuit. Similarly, when the kinase and the phosphatase in the cell state classifier are derived from NarX, NtrB, or PhoR, the activator comprises NarL, NtrC, or PhoB, respectively. One skilled in the art is familiar with activation domains and methods of fusing the RR to the activation domain.

TABLE 2

Non-limiting, Exemplary Response Regulators

| Response Regulators | Amino Acid Sequences |
|---|---|
| OmpR | MQENYKILVVDDDMRLRALLERYLTEQGFQVRSVANAEQ MDRLLTRESFHLMVLDLMLPGEDGLSICRRLRSQSNPMP IIMVTAKGEEVDRIVGLEIGADDYIPKPFNPRELLARIR AVLRRQANELPGAPSQEEAVIAFGKFKLNLGTREMFRED EPMPLTSGEFAVLKALVSHPREPLSRDKLMNLARGREYS AMERSIDVQISRLRRMVEEDPAHPRYIQTVWGLGYVFVP DGSKA (SEQ ID NO: 10) |
| NarL | MSNQEPATILLIDDHPMLRTGVKQLISMAPDITVVGEAS NGEQGIELAESLDPDLILLDLNMPGMNGLETLDKLREKS LSGRIVVFSVSNHEEDVVTALKRGADGYLLKDMEPEDLL KALHQAAAGEMVLSEALTPVLAASLRANRATTERDVNQL TPRERDILKLIAQGLPNKMIARRLDITESTVKVHVKHML KKMKLKSRVEAAVWVHQERIF (SEQ ID NO: 11) |
| NtrC | MQRGIVWVVDDDSSIRWVLERALAGAGLTCTTFENGAEV LEALASKTPDVLLSDIRMPGMDGLALLKQIKQRHPMLPV IIMTAHSDLDAAVSAYQQGAFDYLPKPFDIDEAVALVER AISHYQEQQQPRNVQLNGPTTDIIGEAPAMQDVFRIIGR LSRSSISVLINGESGTGKELVAHALHRHSPRAKAPFIAL NMAAIPKDLIESELFGHEKGAFTGANTIRQGRFEQADGG TLFLDEIGDMPLDVQTRLLRVLADGQFYRVGGYAPVKVD VRIIAATHQNLEQRVQEGKFREDLFHRLNVIRVHLPPLR ERREDIPRLARHFLQVAARELGVEAKLLHPETEAALTRL AWPGNVRQLENTCRWLTVMAAGQEVLIQDLPGELFESTV AESTSQMQPDSWATLLAQWADRALRSGHQNLLSEAQPEL ERTLLTTALRHTQGHKQEAARLLGWGRNTLTRKLKELGM E (SEQ ID NO: 12) |
| PhoB | MARRILVVEDEAPIREMVCFVLEQNGFQPVEAEDYDSAV NQLNEPWPDLILLLDWMLPGGSGIQFIKHLKRESMTRDIP VVMLTARGEEEDRVRGLETGADDYITKPFSPKELVARIK AVMRRISPMAVEEVIEMQGLSLDPTSHRVMAGEEPLEMG PTEFKLLHFFMTHPERVYSREQLLNHVWGTNVYVEDRTV DVHIRRLRKALEPGGHDRMVQTVRGTGYRFSTRF (SEQ ID NO: 13) |

In some embodiments, the activatable promoter of the signal circuit comprises one or more (e.g., 1, 2, 3, 4, 5, 6, 7, 8, 9, 10, or more) response elements that bind to the activator, fused to a minimal promoter. A "minimal promoter" refers to the minimal elements of a promoter that has the promoter function. A minimal promoter typically contains the TATA box and transcription initiation site. Minimal promoters are typically in active unless regulatory elements that enhance promoter activity are placed upstream (e.g., such as the response elements to the RRs, as described herein). In some embodiments, the activatable promoter of the signal circuit comprises one or more (e.g., 1, 2, 3, 4, 5, or more) response elements that bind to the activator. In some embodiments, the activatable promoter of the signal circuit comprises three response elements that bind to the activator. A "response element" is a short sequences of DNA within a gene promoter region that are able to bind specific transcription factors and regulate transcription of genes. Under certain conditions, a transcription activator protein binds to the response element and stimulates transcription. Herein, the activator binds to the response elements in the activatable promoter of the signal circuit, activating the activatable promoter and producing the output molecule. In some embodiments, the activatable promoter comprises one or more (e.g., 1, 2, 3, 4, 5, or more) response elements fused to a minimal protein at the 5' end. In some embodiments, the one or more (e.g., 1, 2, 3, 4, 5, or more) response elements are connected without a nucleotide linker between each response element. In some embodiments, the one or more (e.g., 1, 2, 3, 4, 5, or more) response elements are connected with a nucleotide linker between each response element. In some embodiments, the linker is 2-20 nucleotides long. For example, the linker may be 2, 3, 4, 5, 6, 7, 8, 9, 10, 11, 12, 13, 14, 15, 16, 17, 18, 19, or 20 nucleotides long. Longer or shorter linkers may also be used.

In some embodiments, each of the response element comprises one or more (e.g., 1, 2, 3, 4, 5, 6, 7, 8, 9, 10, or more) operators. In some embodiments, each of the response element comprises 3 operators. An "operator," as used herein, refers to a segment of DNA to which a repressor binds to regulate gene expression by repressing it. In the lac operon, an operator is defined as a segment between the promoter and the genes of the operon. When bound by a repressor, the repressor protein physically obstructs the RNA polymerase from transcribing the genes, thus repressing transcription of the gene.

In some embodiments, the one or more (e.g., 1, 2, 3, 4, 5, 6, 7, 8, 9, 10, or more) operators are connected without a nucleotide spacer between each operator. In some embodiments, the one or more (e.g., 1, 2, 3, 4, 5, 6, 7, 8, 9, 10, or more) operators are connected with a nucleotide spacer between each operator. In some embodiments, the nucleotide spacer is 2-10 nucleotide long. For example, the nucleotide spacer may be 2, 3, 4, 5, 6, 7, 8, 9, or 10 nucleotides long. Longer or shorter nucleotide spacers may also be used. Non-limiting, exemplary RRs and their respective operators are provided in Table 3.

TABLE 3

Non-limiting, Exemplary Response Regulators and Operators

| Name of Response Regulator | Operator Sequence | SEQ ID NO |
|---|---|---|
| OmpR | ATTTACATTTTGAAACATCTA | 14 |
| NarL | TACCGCTATTGAGGTA | 15 |
| NtrC | TGCACTAAAATGGTGCA | 16 |
| PhoB | CTGTCATAWAWCTGTCAY (W is A or T, Y is C or T) | 17 |

In some embodiments, the cell state classifier of the present disclosure further comprises a control circuit. A "control circuit" refers to a circuit that produces a constant signal independent of the input (e.g., the microRNA profile of a cell) and may be used to control for variations caused by other factors other than the microRNA profile, e.g., transfection, cellular health, etc. The control circuit comprises a constitutive promoter operably linked to a nucleotide sequence encoding a control signal that is different from the first output molecule or the second output molecule. The control signal is typically a detectable molecule such as a fluorescent molecule.

Genetic Elements of the Cell State Classifier

Further provided herein are the various genetic elements used in the genetic circuits of the cell state classifier. A "genetic element" refers to a particular nucleotide sequence that has a role in nucleic acid expression (e.g., promoter, enhancer, terminator) or encodes a discrete product of a genetic circuit (e.g., an activator, a microRNA, or an output molecule).

The first and second sensor circuits of the cell state classifier "senses" microRNAs via microRNA target sites present in the sensor circuits. A "microRNA" or "miRNA" is a small non-coding RNA molecule that functions in RNA silencing and post-transcriptional regulation of gene expression (e.g., as described in Ambros et al., Nature 431 (7006): 350-5, 2004; and Bartel et al., Cell. 136 (2): 215-33, 2004). A microRNA may be 15-30 nucleotides in length. For example, a microRNA may be 15-30, 15-25, 15-20, 20-30, 20-25, or 25-30 nucleotides in length. In some embodiments, a microRNA is 16-24 nucleotides in length. In some embodiments, a microRNA is 20-24 nucleotides in length. In some embodiments, a microRNA is 15, 16, 17, 18, 19, 20, 21, 22, 23, 24, 25, 26, 27, 28, 29, or 30 nucleotides in length.

A "microRNA target site" is a nucleotide sequence that is complementary to the nucleotide sequence of the microRNA. Naturally, microRNA targeting sites exist in messenger RNAs (mRNA), typically in the 3' untranslated regions of mRNAs. Binding of the microRNA to its target site in via sequence complementarity leads to silencing of an output molecule either via degrading the mRNA or suppressing translation of the mRNA (e.g., as described in Bartel et al., Cell 136 (2): 215-33 (2009), incorporated herein by reference) containing the microRNA binding sites. Herein, when microRNA target sites are referred in the context of the genetic circuits (i.e., in the context of DNA), it intends to mean the nucleotide sequence that encodes the microRNA target sites in the mRNA that is produced from the genetic circuit. As described herein, designated microRNA target sites are placed either upstream or downstream, or both, of a coding sequence in genetic circuits. As such, when a mRNA is produced from the genetic circuit, the microRNA target sites are present in the 5' UTR or 3' UTR, or both 5' and 3' UTRs in the mRNA.

One skilled in the art is familiar with the mechanism of gene silencing by microRNAs. For example, in the cell state classifier of the present disclosure, if a microRNA is expressed and a sensor circuit (e.g., the first or second sensor circuit) comprise one or more (e.g., 1, 2, 3, 4, 5, 6, 7, 8, 9, 10, or more) targets sites of the microRNA (either upstream or downstream of the coding sequence, or both), the microRNA can bind to the target sites in the mRNA produced by the sensor circuit and mediate the degradation of the mRNA, thus reducing the expression of the protein encoded by the mRNA (translational control). In some embodiments, expression of the protein encoded by the mRNA is reduced by at least 2-fold, at least 5-fold, at least 10-fold, at least 20-fold, at least 30-fold, at least 40-fold, at least 50-fold, at least 60-fold, at least 70-fold, at least 80-fold, at least 90-fold, at least 99-fold, or more compared to when the microRNA is not present. In some embodiments, expression of the protein encoded by the mRNA is no more than 1%, no more than 5%, no more than 10%, no more than 20%, no more than 30%, no more than 40%, no more than 50%, no more than 60%, no more than 70%, no more than 80% of the output molecule when the microRNA is not present. In some embodiments, a higher/lower level of the microRNA results in a higher/lower decrease in the protein encoded by the mRNA containing the microRNA target sites.

Information about the sequences, origins, and functions of known microRNAs maybe found in publically available databases (e.g., mirbase.org/, all versions, as described in Kozomara et al., Nucleic Acids Res 2014 42:D68-D73; Kozomara et al., Nucleic Acids Res 2011 39:D152-D157; Griffiths-Jones et al., Nucleic Acids Res 2008 36:D154-D158; Griffiths-Jones et al., Nucleic Acids Res 2006 34:D140-D144; and Griffiths-Jones et al., Nucleic Acids Res 2004 32:D109-D111, including the most recently released version miRBase 21, which contains "high confidence" microRNAs). Non-limiting examples of microRNAs that are expressed in cells and are able to be detected by the cell state classifier are: FF4, FF5, let-7b, let-7c, let-7d, let-7e, let-7f, let-7g, let-7i, miR-100, miR-103, miR-106a, miR-107, miR-10a, miR-10b, miR-122, miR-125a, miR-125b, miR-126, miR-126*, miR-127-3p, miR-128a, miR-129, miR-133b, miR-135b, miR-137, miR-141, miR-143, miR-145, miR-146a, miR-146b, miR-148a, miR-149, miR-150, miR-155, miR-15a, miR-17-3p, miR-17-5p, miR-181a, miR-181b, miR-181c, miR-183, miR-184, miR-186, miR-187, miR-189, miR-18a, miR-190, miR-191, miR-192, miR-195, miR-197, miR-199a, miR-199a*, miR-19a, miR-19b, miR-200a, miR-200a*, miR-200b, miR-200c, miR-202, miR-203, miR-205, miR-20a, miR-21, miR-210, miR-216, miR-218, miR-22, miR-221, miR-222, miR-223, miR-224, miR-23a, miR-23b, miR-24, miR-25, miR-26a, miR-26b, miR-27a, miR-27b, miR-29a, miR-29b, miR-296-5p, miR-301, miR-302a, miR-302a*, miR-30a, miR-30b, miR-30c, miR-30d, miR-30e-3p, miR-30e-5p, miR-31, miR-320, miR-323, miR-324-5p, miR-326, miR-330, miR-331, miR-335, miR-346, miR-34a, miR-370, miR-372, miR-373, miR-373*, miR-497, miR-498, miR-503, miR-92, miR-93, miR-96, and miR-99a.

In some embodiments, the microRNA detected using the cell state classifier of the present disclosure is selected from: hsa-let-7a-2-3p, hsa-let-7a-3p, hsa-let-7a-5p, hsa-let-7b-3p, hsa-let-7b-5p, hsa-let-7c-5p, hsa-let-7d-3p, hsa-let-7d-5p, hsa-let-7e-3p, hsa-let-7e-5p, hsa-let-7f-1-3p, hsa-let-7f-2-3p, hsa-let-7f-5p, hsa-let-7g-3p, hsa-let-7g-5p, hsa-let-7i-5p, hsa-miR-1, hsa-miR-1-3p, hsa-miR-1-5p, hsa-miR-100-3p, hsa-miR-100-5p, hsa-miR-101-3p, hsa-miR-101-5p, hsa-miR-103a-2-5p, hsa-miR-103a-3p, hsa-miR-105-3p, hsa-miR-105-5p, hsa-miR-106a-3p, hsa-miR-106a-5p, hsa-miR-106b-3p, hsa-miR-106b-5p, hsa-miR-107, hsa-miR-10a-3p, hsa-miR-10a-5p, hsa-miR-10b-3p, hsa-miR-10b-5p, hsa-miR-1185-1-3p, hsa-miR-1185-2-3p, hsa-miR-1185-5p, hsa-miR-122a-5p, hsa-miR-1249-3p, hsa-miR-1249-5p, hsa-miR-124a-3p, hsa-miR-125a-3p, hsa-miR-125a-5p, hsa-miR-125b-1-3p, hsa-miR-125b-2-3p, hsa-miR-125b-5p, hsa-miR-126-3p, hsa-miR-126-5p, hsa-miR-12'7-3p, hsa-miR-1271-3p, hsa-miR-1271-5p, hsa-miR-1278, hsa-miR-128-1-5p, hsa-miR-128-2-5p, hsa-miR-128-3p, hsa-miR-1285-3p, hsa-miR-1285-5p, hsa-miR-1287-3p, hsa-miR-1287-5p, hsa-miR-129-1-3p, hsa-miR-129-2-3p, hsa-miR-129-5p, hsa-miR-1296-3p, hsa-miR-1296-5p, hsa-miR-1304-3p, hsa-miR-1304-5p, hsa-miR-1306-3p, hsa-miR-1306-5p, hsa-miR-1307-3p, hsa-miR-1307-5p, hsa-miR-130a-3p, hsa-miR-130b-3p, hsa-miR-130b-5p, hsa-miR-132-3p, hsa-miR-132-5p, hsa-miR-133a-3p, hsa-miR-133a-5p, hsa-miR-133b, hsa-miR-134-3p, hsa-miR-134-5p, hsa-miR-135a-3p, hsa-miR-135a-5p, hsa-miR-135b-3p, hsa-miR-135b-5p, hsa-miR-136-3p, hsa-miR-136-5p, hsa-miR-138-1-3p, hsa-miR-138-5p, hsa-miR-139-3p, hsa-miR-139-5p, hsa-miR-140-3p, hsa-miR-140-5p, hsa-miR-141-3p, hsa-miR-141-5p, hsa-miR 3p, hsa-miR-142-5p, hsa-miR-143-3p, hsa-miR-143-5p, hsa-miR-144-3p, hsa-miR-144-5p, hsa-miR-145-5p, hsa-miR-146a-3p, hsa-miR-146a-5p, hsa-miR-147a, hsa-miR-148a-3p, hsa-miR-148a-5p, hsa-miR-148b-3p, hsa-miR-148b-5p, hsa-miR-149-3p, hsa-miR-144-3p, hsa-miR-150-3p, hsa-miR-150-5p, hsa-miR-151a-3p, hsa-miR-151a-5p, hsa-miR-152-3p, hsa-miR-152-5p, hsa-miR-154-3p, hsa-miR-154-5p, hsa-miR-155-3p, hsa-miR-155-5p, hsa-miR-15a-3p, hsa-miR-15a-5p, hsa-miR-15b-3p, hsa-miR-15b-5p, hsa-miR-16-1-3p, hsa-miR-16-2-3p, hsa-miR-16-5p, hsa-miR-17-3p, hsa-miR-17-5p, hsa-miR-181a-3p, hsa-miR-181a-5p, hsa-miR-181b-2-3p, hsa-miR-181b-5p, hsa-miR-181c-5p, hsa-miR-181d-3p, hsa-miR-181d-5p, hsa-miR-182-3p, hsa-miR-182-5p, hsa-miR-183-3p, hsa-miR-183-5p, hsa-miR-185-3p, hsa-miR-185-5p, hsa-miR-186-3p, hsa-miR-186-5p, hsa-miR-188-3p, hsa-miR-188-5p, hsa-miR-18a-3p, hsa-miR-18a-5p, hsa-miR-18b-5p, hsa-miR-1908-3p, hsa-miR-1908-5p, hsa-miR-190a-3p, hsa-miR-190a-5p, hsa-miR-191-3p, hsa-miR-191-5p, hsa-miR-1910-3p, hsa-miR-1910-5p, hsa-miR-192-3p, hsa-miR-192-5p, hsa-miR-193a-3p, hsa-miR-193a-5p, hsa-miR-193b-3p, hsa-miR-193b-5p, hsa-miR-194-3p, hsa-miR-194-5p, hsa-miR-195-3p, hsa-miR-195-5p, hsa-miR-196a-3p, hsa-miR-196a-5p, hsa-miR-196b-3p, hsa-miR-196b-5p, hsa-miR-19'7-3p, hsa-miR-19'7-5p, hsa-miR-199a-3p, hsa-miR-199a-5p, hsa-miR-199b-3p, hsa-miR-199b-5p, hsa-miR-19a-3p, hsa-miR-19a-5p, hsa-miR-19b-1-5p, hsa-miR-19b-2-5p, hsa-miR-19b-3p, hsa-miR-200a-3p, hsa-miR-200a-5p, hsa-miR-200b-3p, hsa-miR-200b-5p, hsa-miR-200c-3p, hsa-miR-200c-5p, hsa-miR-202-3p, hsa-miR-202-5p, hsa-miR-203a-3p, hsa-miR-203a-5p, hsa-miR-204-5p, hsa-miR-208b-3p, hsa-miR-208b-5p, hsa-miR-20a-3p, hsa-miR-20a-5p, hsa-miR-20b-3p, hsa-miR-20b-5p, hsa-miR-21-5p, hsa-miR-210-3p, hsa-miR-210-5p, hsa-miR-211-3p, hsa-miR-211-5p, hsa-miR-2116-3p, hsa-miR-2116-5p, hsa-miR-212-3p, hsa-miR-214-3p, hsa-miR-215-5p, hsa-miR-217, JG_miR-218-1-3p, hsa-miR-218-5p, hsa-miR-219a-1-3p, hsa-miR-219a-2-3p, hsa-miR-219a-5p, hsa-miR-219b-3p, hsa-miR-219b-5p, hsa-miR-22-3p, hsa-miR-22-5p, hsa-miR-221-3p, hsa-miR-221-5p, hsa-miR-222-3p, hsa-miR-222-5p, hsa-miR-223-3p, hsa-miR-223-5p, hsa-miR-23a-3p, hsa-miR-23a-5p, hsa-miR-23b-3p, hsa-miR-24-1-5p, hsa-miR-25-3p, hsa-miR-25-5p, hsa-miR-26a-1-3p, hsa-miR-26a-2-3p, hsa-miR-26a-5p, hsa-miR-26b-5p, hsa-miR-27a-3p, hsa-miR-27a-5p, hsa-miR-27b-3p, hsa-miR-27b-5p, hsa-miR-28-3p, hsa-miR-28-5p, hsa-miR-296-3p, hsa-miR-296-5p, hsa-miR-299-3p, hsa-miR-299-5p, hsa-miR-29a-3p, hsa-miR-29a-5p, hsa-miR-29b-1-5p, hsa-miR-29b-3p, hsa-miR-29c-3p, hsa-miR-301a-3p, hsa-miR-301a-5p, hsa-miR-301b-3p, hsa-miR-301b-5p, hsa-miR-302a-3p, hsa-miR-302a-5p, hsa-miR-302b-5p, hsa-miR-302c-3p, hsa-miR-302c-5p, hsa-miR-3065-3p, hsa-miR-3065-5p, hsa-miR-3074-3p, hsa-miR-3074-5p, hsa-miR-30a-3p, hsa-miR-30a-5p, hsa-miR-30b-3p, hsa-miR-30b-5p, hsa-miR-30c-1-3p, hsa-miR-30c-2-3p, hsa-miR-30c-5p, hsa-miR-30d-3p, hsa-miR-30d-5p, hsa-miR-30e-3p, hsa-miR-30e-5p, hsa-miR-31-3p, hsa-miR-31-5p, hsa-miR-3130-3p, hsa-miR-3130-5p, hsa-miR-3140-3p, hsa-miR-3140-5p, hsa-miR-3144-3p, hsa-miR-3144-5p, hsa-miR-3158-3p, hsa-miR-3158-5p, hsa-miR-32-3p, hsa-miR-32-5p, hsa-miR-320a, hsa-miR-323a-3p, hsa-miR-323a-5p, hsa-miR-324-3p, hsa-miR-324-5p, hsa-miR-326, hsa-miR-328-3p, hsa-miR-328-5p, hsa-miR-329-3p, hsa-miR-329-5p, hsa-miR-330-3p, hsa-miR-330-5p, hsa-miR-331-3p, hsa-miR-331-5p, hsa-miR-335-3p, hsa-miR-335-5p, hsa-miR-337-3p, hsa-miR-337-5p, hsa-miR-338-3p, hsa-miR-338-5p, hsa-miR-339-3p, hsa-miR-339-5p, hsa-miR-33a-3p, hsa-miR-33a-5p, hsa-miR-33b-3p, hsa-miR-33b-5p, hsa-miR-340-3p, hsa-miR-340-5p, hsa-miR-342-3p, hsa-miR-342-5p, hsa-miR-345-3p, hsa-miR-345-5p, hsa-miR-34a-3p, hsa-miR-34a-5p, hsa-miR-34b-3p, hsa-miR-34b-5p, hsa-miR-34c-3p, hsa-miR-34c-5p, hsa-miR-3605-3p, hsa-miR-3605-5p, hsa-miR-361-3p, hsa-miR-361-5p, hsa-miR-3613-3p, hsa-miR-3613-5p, hsa-miR-3614-3p, hsa-miR-3614-5p, hsa-miR-362-3p, hsa-miR-362-5p, hsa-miR-363-3p, hsa-miR-363-5p, hsa-miR-365a-3p, hsa-miR-365a-5p, hsa-miR-365b-3p, hsa-miR-365b-5p, hsa-miR-369-3p, hsa-miR-369-5p, hsa-miR-370-3p, hsa-miR-370-5p, hsa-miR-374a-3p, hsa-miR-374a-5p, hsa-miR-374b-3p, hsa-miR-374b-5p, hsa-miR-375, hsa-miR-376a-2-5p, hsamiR-376a-3p, hsa-miR-376a-5p, hsa-miR-376c-3p, hsa-miR-376c-5p, hsa-miR-377-3p, hsa-miR-377-5p, hsa-miR-378a-3p, hsa-miR-378a-5p, hsa-miR-379-3p, hsa-miR-379-5p, hsa-miR-381-3p, hsa-miR-381-5p, hsa-miR-382-3p, hsa-miR-382-5p, hsa-miR-409-3p, hsa-miR-409-5p, hsa-miR-411-3p, hsa-miR-411-5p, hsa-miR-412-3p, hsa-miR-421, hsa-miR-423-3p, hsa-miR-423-5p, hsa-miR-424-3p, hsa-miR-424-5p, hsa-miR-425-3p, hsa-miR-425-5p, hsa-miR-431-3p, hsa-miR-431-5p, hsa-miR-432-5p, hsa-miR-433-3p, hsa-miR-433-5p, hsa-miR-449a, hsa-miR-449b-5p, hsa-miR-450a-1-3p, hsa-miR-450a-2-3p, hsa-miR-450a-5p, hsa-miR-450b-3p, hsa-miR-450b-5p, hsa-miR-451a, hsa-miR-452-3p, hsa-miR-4524a-3p, hsa-miR-4524a-5p, hsa-miR-4536-3p, hsa-miR-4536-5p, hsa-miR-454-3p, hsa-miR-454-5p, hsa-miR-4707-3p, hsa-miR-4707-5p, hsa-miR-4755-3p, hsa-miR-4755-5p, hsa-miR-4787-3p, hsa-miR-4787-5p, hsa-miR-483-3p, hsa-miR-483-5p, hsa-miR-484, hsa-miR-485-3p, hsa-miR-485-5p, hsa-miR-487b-3p, hsa-miR-487b-5p, hsa-miR-488-3p, hsa-miR-488-5p, hsa-miR-489-3p, hsa-miR-490-3p, hsa-miR-490-5p, hsa-miR-491-3p, hsa-miR-491-5p, hsa-miR-493-3p, hsa-miR-493-5p, hsa-miR-494-3p, hsa-miR-494-5p, hsa-miR-495-3p, hsa-miR 5p, hsa-miR-497-3p, hsa-miR-497-5p, hsa-miR-498, hsa-miR-5001-3p, hsa-miR-5001-5p, hsa-miR-500a-3p, hsa-miR-500a-5p, hsa-miR-5010-3p, hsa-miR-5010-5p, hsa-miR-503-3p, hsa-miR-503-5p, hsa-miR-504-3p, hsa-miR-504-5p, hsa-miR-505-3p, hsa-miR-505-5p, hsa-miR-506-3p, hsa-miR-506-5p, hsa-miR-508-3p, hsa-miR-508-5p, hsa-miR-509-3-5p, hsa-miR-509-3p, hsa-miR-509-5p, hsa-miR-510-3p, hsa-miR-510-5p, hsa-miR-512-5p, hsa-miR-513c-3p, hsa-miR-513c-5p, hsa-miR-514a-3p, hsa-miR-514a-5p, hsa-miR-514b-3p, hsa-miR-514b-5p, hsa-miR-516b-5p, hsa-miR-518c-3p, hsa-miR-518f-3p, hsa-miR-5196-3p, hsa-miR-5196-5p, hsa-miR-519a-3p, hsa-miR-519a-5p, hsa-miR-519c-3p, hsa-miR-519e-3p, hsa-miR-520c-3p, hsa-miR-520f-3p, hsa-miR-520g-3p, hsa-miR-520h, hsa-miR-522-3p, hsa-miR-525-5p, hsa-miR-526b-5p, hsa-miR-532-3p, hsa-miR-532-5p, hsa-miR-539-3p, hsa-miR-539-5p, hsa-miR-542-3p, hsa-miR-542-5p, hsa-miR-543, hsa-miR-545-3p, hsa-miR-545-5p, hsa-miR-548a-3p, hsa-miR-548a-5p, hsa-miR-548ar-3p, hsa-miR-548ar-5p, hsa-miR-548b-3p, hsa-miR-548d-3p, hsa-miR-548d-5p, hsa-miR-548e-3p, hsa-miR-548e-5p, hsa-miR-548h-3p, hsa-miR-548h-5p, hsa-miR-548j-3p, hsa-miR-548j-5p, hsa-miR-548o-3p, hsa-miR-548o-5p, hsa-miR-548v, hsa-miR-551b-3p, hsa-miR-551b-5p, hsa-miR-552-3p, hsa-miR-556-3p, hsa-miR-556-5p, hsa-miR-561-3p, hsa-miR-561-5p, hsa-miR-562, hsa-miR-567, hsa-miR-569, hsa-miR-570-3p, hsa-miR-570-5p, hsa-miR-571, hsa-miR-574-3p, hsa-miR-574-5p, hsa-miR-576-3p, hsa-miR-576-5p, hsa-miR-577, hsa-miR-579-3p, hsa-miR-579-5p, hsa-miR-582-3p, hsa-miR-582-5p, hsa-miR-584-3p, hsa-miR-584-5p, hsa-miR-589-3p, hsa-miR-589-5p, hsa-miR-590-3p, hsa-miR-590-5p, hsa-miR-595, hsa-miR-606, hsa-miR-607, hsa-miR-610, hsa-miR-615-3p, hsa-miR-615-5p, hsa-miR-616-3p, hsa-miR-616-5p, hsa-miR-617, hsa-miR-619-5p, hsa-miR-624-3p, hsa-miR-624-5p, hsa-miR-625-3p, hsa-miR-625-5p, hsa-miR-62'7-3p, hsa-miR-627-5p, hsa-miR-628-3p, hsa-miR-628-5p, hsa-miR-629-3p, hsa-miR-629-5p, hsa-miR-630, hsa-miR-633, hsa-miR-634, hsa-miR-635, hsa-miR-636, hsa-miR-640, hsa-miR-642a-3p, hsa-miR-642a-5p, hsa-miR-643, hsa-miR-645, hsa-miR-648, hsa-miR-6503-3p, hsa-miR-6503-5p, hsa-miR-651-3p, hsa-miR-651-5p, hsa-miR-6511a-3p, hsa-miR-6511a-5p, hsa-miR-652-3p, hsa-miR-652-5p, hsa-miR-653-5p, hsa-miR-654-3p, hsa-miR-654-5p, hsa-miR-657, hsa-miR-659-3p, hsa-miR-660-3p, hsa-miR-660-5p, hsa-miR-664b-3p, hsa-miR-664b-5p, hsa-miR-671-3p, hsa-miR-671-5p, hsa-miR-675-3p, hsa-miR-675-5p, hsa-miR-7-1-3p, hsa-miR-7-5p, hsa-miR-708-3p, hsa-miR-708-5p, hsa-miR-744-3p, hsa-miR-744-5p, hsa-miR-758-3p, hsa-miR-758-5p, hsa-miR-765, hsa-miR-766-3p, hsa-miR-766-5p, hsa-miR-767-3p, hsa-miR-767-5p, hsa-miR-769-3p, hsa-miR-769-5p, hsa-miR-802, hsa-miR-873-3p, hsa-miR-873-5p, hsa-miR-874-3p, hsa-miR-874-5p, hsa-miR-876-3p, hsa-miR-876-5p, hsa-miR-885-3p, hsa-miR-885-5p, hsa-miR-887-3p, hsa-miR-887-5p, hsa-miR-9-3p, hsa-miR-9-5p, hsa-miR-92a-1-5p, hsa-miR-92a-2-5p, hsa-miR-92a-3p, hsa-miR-92b-3p, hsa-miR-92b-5p, hsa-miR-93-3p, hsa-miR-93-5p, hsa-miR-941, hsa-miR-942-3p, hsa-miR-942-5p, hsa-miR-96-3p, hsa-miR-96-5p, hsa-miR-98-3p, hsa-miR-98-5p, hsa-miR-99a-3p, hsa-miR-99a-5p, hsa-miR-99b-3p, and hsa-miR-99b-5p.

In some embodiments, the cell state classifier of the present disclosure is used in a bacterial cell. Though naturally-occurring bacterial cells lack true miRNAs (e.g., as described in Tjaden et al., Nucleic Acids Res. 34 (9): 2791-802), short non-coding RNA sequences have been identified in bacterial genome that broadly have comparable function as eukaryotic miRNAs. Such bacterial short non-coding RNAs function similarly as the miRNAs of the present disclosure and may be detected by the cell state classifier described herein.

For classifying a cell type (e.g., a cancer cell), one skilled in the art is familiar with the microRNAs that express specifically in such cell type but not in other cell types, and their respective nucleotide sequences. One skilled in the art is also familiar with the designing the target sites for the microRNA to be detected. Non-limiting, exemplary microRNA and respective target site sequences are provided in Table 4.

TABLE 4

Non-limiting, Exemplary Synthetic microRNA and Target Sites

| microRNA Name | Nucleotide Sequence Encoding microRNA | Target Sequence |
| --- | --- | --- |
| FF3 | TTTGTATTCAGCCCATATCG (SEQ ID NO: 18) | AACGATATGGGCTGAATACAAA (SEQ ID NO: 19) |
| FF4 | TTTAATTAAAGACTTCAAGCG (SEQ ID NO: 20) | CCGCTTGAAGTCTTTAATTAAA (SEQ ID NO: 21) |
| FF5 | TAATTGTCAAATCAGAGTGC (SEQ ID NO: 22) | AAGCACTCTGATTTGACAATTA (SEQ ID NO: 23) |
| FF6 | TTTATGAGGAATCTCTTTGG (SEQ ID NO: 24) | AACCAAAGAGATTCCTCATAAA (SEQ ID NO: 25) |
| T1 | TTCGAAGTATTCCGCGTACG (SEQ ID NO: 26) | CACGTACGCGGAATACTTCGAA (SEQ ID NO: 27) |

One or more (e.g., 1, 2, 3, 4, 5, 6, 7, 8, 9, 10, or more) target sites of the microRNAs to be detected by the cell state classifier are placed in each circuit (e.g., first or second sensor circuit, signal circuit, etc.) in a non-coding region, e.g., upstream and/or downstream of the nucleotide sequence encoding the protein that is produced by the circuit (e.g., activator, repressor, or output molecule). Being "upstream" means the microRNA target sites are placed 5' of the nucleotide sequence encoding the protein that is produced by the circuit (e.g., activator, repressor, or output molecule). Being "downstream" means the microRNA target sites are placed 3' of the nucleotide sequence encoding the protein that is produced by the circuit (e.g., activator, repressor, or output molecule).

In some embodiments, one or more (e.g., 1, 2, 3, 4, 5, 6, 7, 8, 9, 10, or more) microRNA target sites are placed upstream of and is immediately adjacent to (no nucleotides in between) the nucleotide sequence encoding the protein that is produced by the circuit (e.g., activator or output molecule). In some embodiments, one or more (e.g., 1, 2, 3, 4, 5, 6, 7, 8, 9, 10, or more) microRNA target sites are placed upstream of and is separated by a nucleotide spacer from the nucleotide sequence encoding the protein that is produced by the circuit (e.g., activator, kinase, phosphatase, or output molecule). In some embodiments, the nucleotide spacer is 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used.

In some embodiments, one or more (e.g., 1, 2, 3, 4, 5, 6, 7, 8, 9, 10, or more) microRNA target sites are placed downstream of and is immediately adjacent to (no nucleotides in between) the nucleotide sequence encoding the protein that is produced by the circuit (e.g., activator, kinase, phosphatase, or output molecule). In some embodiments, one or more (e.g., 1, 2, 3, 4, 5, 6, 7, 8, 9, 10, or more) microRNA target sites are placed downstream of and is separated by a nucleotide spacer from the nucleotide sequence encoding the protein that is produced by the circuit (e.g., activator, kinase, phosphatase, or output molecule). In some embodiments, the nucleotide spacer is 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used.

In some embodiments, one or more (e.g., 1, 2, 3, 4, 5, 6, 7, 8, 9, 10, or more) microRNA target sites are placed upstream and/or downstream of and is immediately adjacent (no nucleotides in between) to the nucleotide sequence encoding the protein that is produced by the circuit (e.g., activator, kinase, phosphatase, or output molecule). In some embodiments, one or more (e.g., 1, 2, 3, 4, 5, 6, 7, 8, 9, 10, or more) microRNA target sites are placed upstream and/or downstream of and is separated by a nucleotide spacer from the nucleotide sequence encoding the protein that is produced by the circuit (e.g., activator, kinase, phosphatase, or output molecule). In some embodiments, the nucleotide spacer is 1-20 nucleotides long. For example, the nucleotide spacer may be 1, 2, 3, 4, 5, 6, 7, 8, 9, 10, 11, 12, 13, 14, 15, 16, 17, 18, 19, or 20 nucleotides long. Nucleotide spacers longer than 20 nucleotide may also be used. In some embodiments, placing multiple microRNA target sites at different locations of each circuit strengthens (e.g., by at least 30%) the inhibitory effect of the microRNA on the product of the circuit. When multiple microRNA target sites are used, there may be a nucleotide spacer (e.g., a nucleotide spacer of 1, 2, 3, 4, 5, 6, 7, 8, 9, or 10 nucleotides long), or no space between each target site.

An "activator," as used herein, refers to a transcriptional activator. The terms "activator" or "transcriptional activator" are used interchangeably herein. A transcriptional activator is a protein that increases gene transcription of a gene or set of genes. Most activators function by binding sequence-specifically to a DNA site located in or near a promoter and making protein-protein interactions with the general transcription machinery (RNA polymerase and general transcription factors), thereby facilitating the binding of the general transcription machinery to the promoter.

Herein, the expression of a gene is considered to be "activated" by an activator if the expression of the genes is at least 20% higher in the presence of the activator, compared to without the activator. For example, the expression of a gene is considered to be activated by an activator if the expression of the genes is at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher in the presence of the activator, compared to without the activator. In some embodiments, the expression of a gene is considered to be activated by an activator if the expression of the genes is 20%, 30%, 40%, 50%, 60%, 70%, 80%, 90%, 100%, 2-fold, 5-fold, 10-fold, 100-fold, 1000-fold, or higher in the presence of the activator, compared to without the activator.

One skilled in the art is able to choose the transcriptional activators or repressors for use in accordance with the present disclosure. Public databases are available for known or predicted transcriptional regulators, e.g., transcriptionfactor.org.

An "output molecule," as used herein, refers to a signal produced by the cell state classifier after detecting the microRNA profile (e.g., a matching microRNA profile). The cell state classifier of the present disclosure is designed such that the output molecule is expressed when a matching microRNA profile is detected. In some embodiments, the output molecule has a basal expression level and the expression level increases (e.g., by at least 20%) when a matching microRNA profile is detected, compared to when a non-matching microRNA profile is detected. For example, the expression level of the output molecule may be at least 20%, at least 30%, at least 40%, at least 50%, at least 60%, at least 70%, at least 80%, at least 90%, at least 100%, at least 2-fold, at least 5-fold, at least 10-fold, at least 100-fold, at least 1000-fold, or higher when a matching microRNA profile is detected, compared to when a non-matching microRNA profile is detected. In some embodiments, the expression level of the output molecule is 20%, 30%, 40%, 50%, 60%, 70%, 80%, 90%, 100%, 2-fold, 5-fold, 10-fold, 100-fold, 1000-fold, or higher when a matching microRNA profile is detected, compared to when a non-matching microRNA profile is detected.

The output molecule, in some embodiments, is a detectable protein. In some embodiments, a detectable protein is a fluorescent protein. A fluorescent protein is a protein that emits a fluorescent light when exposed to a light source at an appropriate wavelength (e.g., light in the blue or ultraviolet range). Suitable fluorescent proteins that may be used in accordance with the present disclosure include, without limitation, eGFP, eYFP, eCFP, mKate2, mCherry, mPlum, mGrape2, mRaspberry, mGrape1, mStrawberry, mTangerine, mBanana, and mHoneydew. In some embodiments, a detectable protein is an enzyme that hydrolyzes an substrate to produce a detectable signal (e.g., a chemiluminescent signal). Such enzymes include, without limitation, beta-galactosidase (encoded by LacZ), horseradish peroxidase, or luciferase. In some embodiments, the output molecule is a fluorescent RNA. A fluorescent RNA is an RNA aptamer that emits a fluorescent light when bound to a fluorophore and exposed to a light source at an appropriate wavelength (e.g., light in the blue or ultraviolet range). Suitable fluorescent RNAs that may be used as an output molecule in the sensor circuit of the present disclosure include, without limitation, Spinach and Broccoli (e.g., as described in Paige et al., Science Vol. 333, Issue 6042, pp. 642-646, 2011, incorporated herein by reference).

In some embodiments, the output molecule is a therapeutic molecule. A "therapeutic molecule" is a molecule that has therapeutic effects on a disease or condition, and may be used to treat a diseases or condition. Therapeutic molecules of the present disclosure may be nucleic acid-based or protein or polypeptide-based.

In some embodiments, nucleic acid-based therapeutic molecule is an RNA interference (RNAi) molecule (e.g., a microRNA, siRNA, or shRNA) or an nucleic acid enzyme (e.g., a ribozyme). RNAi molecules and there use in silencing gene expression are familiar to those skilled in the art. In some embodiments, the RNAi molecule targets an oncogene. An oncogene is a gene that in certain circumstances can transform a cell into a tumor cell. An oncogene may be a gene encoding a growth factor or mitogen (e.g., c-Sis), a receptor tyrosine kinase (e.g., EGFR, PDGFR, VEGFR, or HER2/neu), a cytoplasmic tyrosine kinase (e.g., Src family kinases, Syk-ZAP-70 family kinases, or BTK family kinases), a cytoplasmic serine/threonine kinase or their regulatory subunits (e.g., Raf kinase or cyclin-dependent kinase), a regulatory GTPase (e.g., Ras), or a transcription factor (e.g., Myc). In some embodiments, the oligonucleotide targets Lipocalin (Lcn2) (e.g., a Lcn2 siRNA). One skilled in the art is familiar with genes that may be targeted for the treatment of cancer.

Non-limiting examples of protein or polypeptide-based therapeutic molecules include enzymes, regulatory proteins (e.g., immuno-regulatory proteins), antigens, antibodies or antibody fragments, and structural proteins. In some embodiments, the protein or polypeptide-based therapeutic molecules are for cancer therapy.

Suitable enzymes (for operably linking to a synthetic promoter) for some embodiments of this disclosure include, for example, oxidoreductases, transferases, polymerases, hydrolases, lyases, synthases, isomerases, and ligases, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, alginase, digestive lipases (e.g., lingual lipase, pancreatic lipase, phospholipase), amylases, cellulases, lysozyme, proteases (e.g., pepsin, trypsin, chymotrypsin, carboxypeptidase, elastase), esterases (e.g. sterol esterase), disaccharidases (e.g., sucrase, lactase, beta-galactosidase, maltase, isomaltase), DNases, and RNases.

Non-limiting examples of antibodies and fragments thereof include: bevacizumab (AVASTIN®), trastuzumab (HERCEPTIN®), alemtuzumab (CAMPATH®, indicated for B cell chronic lymphocytic leukemia), gemtuzumab (MYLOTARG®, hP67.6, anti-CD33, indicated for leukemia such as acute myeloid leukemia), rituximab (RITUXAN®), tositumomab (BEXXAR®, anti-CD20, indicated for B cell malignancy), MDX-210 (bispecific antibody that binds simultaneously to HER-2/neu oncogene protein product and type I Fc receptors for immunoglobulin G (IgG) (Fc gamma RI)), oregovomab (OVAREX®, indicated for ovarian cancer), edrecolomab (PANOREX®), daclizumab (ZENAPAX®), palivizumab (SYNAGIS®, indicated for respiratory conditions such as RSV infection), ibritumomab tiuxetan (ZEVALIN®, indicated for Non-Hodgkin's lymphoma), cetuximab (ERBITUX®), MDX-447, MDX-22, MDX-220 (anti-TAG-72), IOR-05, IOR-T6 (anti-CD1), IOR EGF/R3, celogovab (ONCOSCINT® OV103), epratuzumab (LYMPHOCIDE®), pemtumomab (THERAGYN®), Gliomab-H (indicated for brain cancer, melanoma). In some embodiments, the antibody is an antibody that inhibits an immune check point protein, e.g., an anti-PD-1 antibody such as pembrolizumab (Keytruda®) or nivolumab (Opdivo®), or an anti-CTLA-4 antibody such as ipilimumab (Yervoy®). Other antibodies and antibody fragments may be operably linked to a synthetic promoter, as provided herein.

A regulatory protein may be, in some embodiments, a transcription factor or a immunoregulatory protein. Non-limiting, exemplary transcriptional factors include: those of the NFkB family, such as Rel-A, c-Rel, Rel-B, p50 and p52; those of the AP-1 family, such as Fos, FosB, Fra-1, Fra-2, Jun, JunB and JunD; ATF; CREB; STAT-1, -2, -3, -4, -5 and -6; NFAT-1, -2 and -4; MAF; Thyroid Factor; IRF; Oct-1 and -2; NF-Y; Egr-1; and USF-43, EGR1, Sp1, and E2F1. Other transcription factors may be operably linked to a synthetic promoter, as provided herein.

As used herein, an immunoregulatory protein is a protein that regulates an immune response. Non-limiting examples of immunoregulatory include: antigens, adjuvants (e.g., flagellin, muramyl dipeptide), cytokines including interleukins (e.g., IL-2, IL-7, IL-15 or superagonist/mutant forms of these cytokines), IL-12, IFN-gamma, IFN-alpha, GM-CSF, FLT3-ligand), and immunostimulatory antibodies (e.g., anti-CTLA-4, anti-CD28, anti-CD3, or single chain/antibody fragments of these molecules). Other immunoregulatory proteins may be operably linked to a synthetic promoter, as provided herein.

As used herein, an antigen is a molecule or part of a molecule that is bound by the antigen-binding site of an antibody. In some embodiments, an antigen is a molecule or moiety that, when administered to or expression in the cells of a subject, activates or increases the production of antibodies that specifically bind the antigen. Antigens of pathogens are well known to those of skill in the art and include, but are not limited to parts (coats, capsules, cell walls, flagella, fimbriae, and toxins) of bacteria, viruses, and other microorganisms. Examples of antigens that may be used in accordance with the disclosure include, without limitation, cancer antigens, self-antigens, microbial antigens, allergens and environmental antigens. Other antigens may be operably linked to a synthetic promoter, as provided herein.

In some embodiments, the antigen of the present disclosure is a cancer antigen. A cancer antigen is an antigen that is expressed preferentially by cancer cells (i.e., it is expressed at higher levels in cancer cells than on non-cancer cells) and, in some instances, it is expressed solely by cancer cells. Cancer antigens may be expressed within a cancer cell or on the surface of the cancer cell. Cancer antigens that may be used in accordance with the disclosure include, without limitation, MART-1/Melan-A, gp100, adenosine deaminase-binding protein (ADAbp), FAP, cyclophilin b, colorectal associated antigen (CRC)-C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4 and MAGE-05. The cancer antigen may be selected from the group consisting of GAGE-1, GAGE-2, GAGE-3, GAGE-4, GAGE-5, GAGE-6, GAGE-7, GAGE-8 and GAGE-9. The cancer antigen may be selected from the group consisting of BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pme1117, PRAME, NY-ESO-1, cdc27, adenomatous polyposis coli protein (APC), fodrin, Connexin 37, Ig-idiotype, p15, gp75, GM2 ganglioside, GD2 ganglioside, human papilloma virus proteins, Smad family of tumor antigens, lmp-1, PIA, EBV-encoded nuclear antigen (EBNA)-1, brain glycogen phosphorylase, SSX-1, SSX-2 (HOM-MEL-40), SSX-3, SSX-4, SSX-5, SCP-1 and CT-7, CD20 and c-erbB-2. Other cancer antigens may be operably linked to a synthetic promoter, as provided herein.

In some embodiments, a protein or polypeptide-based therapeutic molecule is a fusion protein. A fusion protein is a protein comprising two heterologous proteins, protein domains, or protein fragments, that are covalently bound to each other, either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

A "promoter" refers to a control region of a nucleic acid sequence at which initiation and rate of transcription of the remainder of a nucleic acid sequence are controlled. A promoter drives expression or drives transcription of the nucleic acid sequence that it regulates. A promoter may also contain sub-regions at which regulatory proteins and molecules may bind, such as RNA polymerase and other transcription factors. Promoters may be constitutive, inducible, activatable, repressible, tissue-specific or any combination thereof. A promoter is considered to be "operably linked" when it is in a correct functional location and orientation in relation to a nucleic acid sequence it regulates to control ("drive") transcriptional initiation and/or expression of that sequence.

A promoter may be one naturally associated with a gene or sequence, as may be obtained by isolating the 5' non-coding sequences located upstream of the coding segment of a given gene or sequence. Such a promoter can be referred to as "endogenous."

In some embodiments, a coding nucleic acid sequence is positioned under the control of a recombinant or heterologous promoter, which refers to a promoter that is not normally associated with the encoded sequence in its natural environment. Such promoters may include promoters of other genes; promoters isolated from any other cell; and synthetic promoters or enhancers that are not "naturally occurring" such as, for example, those that contain different elements of different transcriptional regulatory regions and/or mutations that alter expression through methods of genetic engineering that are known in the art. In addition to producing nucleic acid sequences of promoters and enhancers synthetically, sequences may be produced using recombinant cloning and/or nucleic acid amplification technology, including polymerase chain reaction (PCR) (see U.S. Pat. Nos. 4,683,202 and 5,928,906).

In some embodiments, a promoter is an "inducible promoter," which refer to a promoter that is characterized by regulating (e.g., initiating or activating) transcriptional activity when in the presence of, influenced by or contacted by an inducer signal. An inducer signal may be endogenous or a normally exogenous condition (e.g., light), compound (e.g., chemical or non-chemical compound) or protein that contacts an inducible promoter in such a way as to be active in regulating transcriptional activity from the inducible promoter. Thus, a "signal that regulates transcription" of a nucleic acid refers to an inducer signal that acts on an inducible promoter. A signal that regulates transcription may activate or inactivate transcription, depending on the regulatory system used. Activation of transcription may involve directly acting on a promoter to drive transcription or indirectly acting on a promoter by inactivation a repressor that is preventing the promoter from driving transcription. Conversely, deactivation of transcription may involve directly acting on a promoter to prevent transcription or indirectly acting on a promoter by activating a repressor that then acts on the promoter.

The administration or removal of an inducer signal results in a switch between activation and inactivation of the transcription of the operably linked nucleic acid sequence. Thus, the active state of a promoter operably linked to a nucleic acid sequence refers to the state when the promoter is actively regulating transcription of the nucleic acid sequence (i.e., the linked nucleic acid sequence is expressed). Conversely, the inactive state of a promoter operably linked to a nucleic acid sequence refers to the state when the promoter is not actively regulating transcription of the nucleic acid sequence (i.e., the linked nucleic acid sequence is not expressed).

An inducible promoter of the present disclosure may be induced by (or repressed by) one or more physiological condition(s), such as changes in light, pH, temperature, radiation, osmotic pressure, saline gradients, cell surface binding, and the concentration of one or more extrinsic or intrinsic inducing agent(s). An extrinsic inducer signal or inducing agent may comprise, without limitation, amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones or combinations thereof.

Inducible promoters of the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, an inducer signal of the present disclosure is an N-acyl homoserine lactone (AHL), which is a class of signaling molecules involved in bacterial quorum sensing. Quorum sensing is a method of communication between bacteria that enables the coordination of group based behavior based on population density. AHL can diffuse across cell membranes and is stable in growth media over a range of pH values. AHL can bind to transcriptional activators such as LuxR and stimulate transcription from cognate promoters.

In some embodiments, an inducer signal of the present disclosure is anhydrotetracycline (aTc), which is a derivative of tetracycline that exhibits no antibiotic activity and is designed for use with tetracycline-controlled gene expression systems, for example, in bacteria.

In some embodiments, an inducer signal of the present disclosure is isopropyl β-D-1-thiogalactopyranoside (IPTG), which is a molecular mimic of allolactose, a lactose metabolite that triggers transcription of the lac operon, and it is therefore used to induce protein expression where the gene is under the control of the lac operator. IPTG binds to the lac repressor and releases the tetrameric repressor from the lac operator in an allosteric manner, thereby allowing the transcription of genes in the lac operon, such as the gene coding for beta-galactosidase, a hydrolase enzyme that catalyzes the hydrolysis of β-galactosides into monosaccharides. The sulfur (S) atom creates a chemical bond which is non-hydrolyzable by the cell, preventing the cell from metabolizing or degrading the inducer. IPTG is an effective inducer of protein expression, for example, in the concentration range of 100 µM to 1.0 mM. Concentration used depends on the strength of induction required, as well as the genotype of cells or plasmid used. If lacIq, a mutant that over-produces the lac repressor, is present, then a higher concentration of IPTG may be necessary. In blue-white screen, IPTG is used together with X-gal. Blue-white screen allows colonies that have been transformed with the recombinant plasmid rather than a non-recombinant one to be identified in cloning experiments.

Other inducible promoter systems are known in the art and may be used in accordance with the present disclosure.

In some embodiments, inducible promoters of the present disclosure are from prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated σ70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rhl), Pu, FecA, pRE, cadC, hns, pLas, pLux), σS promoters (e.g., Pdps), σ32 promoters (e.g., heat shock) and σ54 promoters (e.g., glnAp2); negatively regulated *E. coli* promoters such as negatively regulated σ70 promoters (e.g., Promoter (PRM+), modified lamdba Prm promoter, TetR-TetR-4C P(Las) TetO, P(Las) CIO, P(Lac) IQ, RecA_Dlex-O_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLaclq, rrnB P1, cadC, hns, PfhuA, pBad/araC, nhaA, OmpF, RcnR), GS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated *B. subtilis* promoters such as repressible *B. subtilis* σA promoters (e.g., Gram-positive IPTG-inducible, Xyl, hyper-spank) and σB promoters. Other inducible microbial promoters may be used in accordance with the present disclosure.

The different genetic circuits of the cell state classifier may be included in one or more (e.g., 2, 3, or more) nucleic acid molecules (e.g., vectors) and introduced into a cell. A "nucleic acid" is at least two nucleotides covalently linked together, and in some instances, may contain phosphodiester bonds (e.g., a phosphodiester "backbone"). A nucleic acid may be DNA, both genomic and/or cDNA, RNA or a hybrid, where the nucleic acid contains any combination of deoxyribonucleotides and ribonucleotides (e.g., artificial or natural), and any combination of bases, including uracil, adenine, thymine, cytosine, guanine, inosine, xanthine, hypoxanthine, isocytosine and isoguanine. Nucleic acids of the present disclosure may be produced using standard molecular biology methods (see, e.g., Green and Sambrook, *Molecular Cloning, A Laboratory Manual*, 2012, Cold Spring Harbor Press).

In some embodiments, nucleic acids are produced using GIBSON ASSEMBLY® Cloning (see, e.g., Gibson, D. G. et al. *Nature Methods*, 343-345, 2009; and Gibson, D. G. et al. *Nature Methods*, 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies.

In some embodiments, different genetic circuits of the cell state classifier are is delivered to a cell on one or more (e.g., 2, 3, 4, 5, 6, 7, 8, 9, 10, or more) vectors. A "vector" refers to a nucleic acid (e.g., DNA) used as a vehicle to artificially carry genetic material (e.g., an engineered nucleic acid) into a cell where, for example, it can be replicated and/or expressed. In some embodiments, a vector is an episomal vector (see, e.g., Van Craenenbroeck K. et al. *Eur. J. Biochem.* 267, 5665, 2000, incorporated by reference herein). A non-limiting example of a vector is a plasmid. Plasmids are double-stranded generally circular DNA sequences that are capable of automatically replicating in a host cell. Plasmid vectors typically contain an origin of replication that allows for semi-independent replication of the plasmid in the host and also the transgene insert. Plasmids may have more features, including, for example, a "multiple cloning site," which includes nucleotide overhangs for insertion of a nucleic acid insert, and multiple restriction enzyme consensus sites to either side of the insert. Another non-limiting example of a vector is a viral vector (e.g., retroviral, adenoviral, adeno-association, helper-dependent adenoviral systems, hybrid adenoviral systems, herpes simplex, pox virus, lentivirus, Epstein-Barr virus). In some embodiments, the viral vector is derived from an adeno-associated virus (AAV). In some embodiments, the viral vector is derived from an herpes simplex virus (HSV).

The nucleic acids or vectors containing the genetic circuits of the cell state classifier may be delivered to a cell by any methods known in the art for delivering nucleic acids. For example, for delivering nucleic acids to a prokaryotic cell, the methods include, without limitation, transformation, transduction, conjugation, and electroporation. For delivering nucleic acids to a eukaryotic cell, methods include, without limitation, transfection, electroporation, and using viral vectors.

Cells containing the cell state classifiers are also provided herein. A "cell" is the basic structural and functional unit of all known independently living organisms. It is the smallest unit of life that is classified as a living thing. Some organisms, such as most bacteria, are unicellular (consist of a single cell). Other organisms, such as humans, are multicellular.

In some embodiments, a cell for use in accordance with the present disclosure is a prokaryotic cell, which may comprise a cell envelope and a cytoplasmic region that contains the cell genome (DNA) and ribosomes and various sorts of inclusions. In some embodiments, the cell is a bacterial cell. As used herein, the term "bacteria" encompasses all variants of bacteria, for example, prokaryotic organisms and cyanobacteria. Bacteria are small (typical linear dimensions of around 1 micron), non-compartmentalized, with circular DNA and ribosomes of 70S. The term bacteria also includes bacterial subdivisions of Eubacteria and Archaebacteria. Eubacteria can be further subdivided into gram-positive and gram-negative Eubacteria, which depend upon a difference in cell wall structure. Also included herein are those classified based on gross morphology alone (e.g., cocci, bacilli). In some embodiments, the bacterial cells are gram-negative cells, and in some embodiments, the bacterial cells are gram-positive cells. Examples of bacterial cells that may be used in accordance with the invention include, without limitation, cells from *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp. In some embodiments, the bacterial cells are from *Staphylococcus aureus, Bacillus subtilis, Clostridium butyricum, Brevibacterium lactofermentum, Streptococcus agalactiae, Lactococcus lactis, Leuconostoc lactis, Streptomyces, Actinobacillus actinobycetemcomitans, Bacteroides,* cyanobacteria, *Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus* planta rum, *Streptococcus faecalis, Bacillus coagulans, Bacillus ceretus, Bacillus popillae, Synechocystis* strain PCC6803, *Bacillus liquefaciens, Pyrococcus abyssi, Selenomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, Streptomyces ghanaenis, Halobacterium* strain GRB, or *Halobaferax* sp. strain Aa2.2.

In some embodiments, a cell for use in accordance with the present disclosure is a eukaryotic cell, which comprises membrane-bound compartments in which specific metabolic activities take place, such as a nucleus. Examples of eukaryotic cells for use in accordance with the invention include, without limitation, mammalian cells, insect cells, yeast cells (e.g., *Saccharomyces cerevisiae*) and plant cells. In some embodiments, the eukaryotic cells are from a vertebrate animal. In some embodiments, the cell is a mammalian cell. In some embodiments, the cell is a human cell. In some embodiments, the cell is from a rodent, such as a mouse or a rat. Examples of vertebrate cells for use in accordance with the present disclosure include, without limitation, reproductive cells including sperm, ova and embryonic cells, and non-reproductive cells, including kidney, lung, spleen, lymphoid, cardiac, gastric, intestinal, pancreatic, muscle, bone, neural, brain and epithelial cells. Stem cells, including embryonic stem cells, can also be used.

In some embodiments, the cell is a diseased cell. A "diseased cell," as used herein, refers to a cell whose biological functionality is abnormal, compared to a non-diseased (normal) cell. In some embodiments, the diseased cell is a cancer cell.

Functionality of the Cell State Classifier

Some aspects of the present disclosure provide the functionality of the cell state classifiers and methods of using them. In some embodiments, the methods comprise delivering the cell state classifier described herein into a cell in vitro, ex vivo or in vivo (e.g., by any of the methods described herein and known to one skilled in the art). In some embodiments, the methods comprise maintaining the cell containing the cell state classifier, such as by culturing a cell in vitro or ex vivo, or by maintaining the viability of the cell in vivo. In some embodiments, the maintaining is carried out under conditions to allow the cell state classifier to function. In some embodiments, the presence of the cell state classifier in the cell does not change the native microRNA profile of the cell.

Once introduced to a cell that has a microRNA profile, the cell state classifier described herein is able to detect the microRNAs in the cell and produce an output (e.g., a detectable molecule or a therapeutic molecule) accordingly. In some embodiments, no microRNA input is detected, for example, if none of the microRNAs the cell state classifier designed to detected (either microRNA-high or microRNA-low) expresses (e.g., expression level is not detectable). As such, the activator and the kinase of the first sensor circuit are expressed in the absence of microRNA-low inhibition, leading to phosphorylation of the activator. Further, in the absence of the microRNA-high, the phosphatase expresses, dephosphorylating the activator. Thus, a competition exists between phosphorylating and dephosphorylating the activator. It is to be understood that in such situations, the phosphatase dominates, and the activator remains unphosphorylated. The unphosphorylated activator does not bind or activate the activatable promoter in the signal circuit, leading to no production of the output molecule.

In some embodiments, the first microRNA (microRNA-low) expresses (e.g., has a detectable expression level by the cell state classifier), and the activator and the kinase in the first sensor circuit does not express because the first microRNA mediate the degradation of the mRNA encoding the activator and the kinase (translational control). As such, the activatable promoter of the signal circuit is not activated, leading to no expression of the first output molecule.

In contrast, in some embodiments, the first microRNA (microRNA-low) does not express (e.g., has a detectable expression level by the cell state classifier), and the activator and the kinase in the first sensor circuit express. The kinase phosphorylates the activator, causing a conformational change in the activator that allows it to bind the activatable promoter of the signal circuit, activating the expression of the output molecule.

In some embodiments, the second microRNA (microRNA-high) expresses (e.g., has a detectable expression level by the cell state classifier), and phosphatase does not express, because the second microRNA mediates the degradation of the mRNA encoding the phosphatase (translational control). As a result, the activator remains phosphorylated and activates the expression of the output molecule.

In some embodiments, both the first microRNA (microRNA-low) and the second microRNA (microRNA-high) express, repressing the expression of the activator, the kinase, and the phosphatase (e.g., via microRNA binding sites in the first and second sensor circuits). As a result, the activatable promoter in the signal circuit remains inactive due to the lack of the phosphorylated activator, leading to no expression of the output molecule.

As such, the cell state classifier also has a logic function, where the cell state classifier produces an output molecule only when a matching microRNA profile is detected. A matching microRNA profile means the first microRNA (microRNA-low) does not express (e.g., undetectable by the cell state classifier), and the second microRNA (microRNA-high) expresses (e.g., at least detectable by the cell state classifier), and the output molecule is produced. In some embodiments, the first microRNA (microRNA low) expresses (e.g., expression level is detectable by the cell state classifier) or has high expression level, and the second microRNA (microRNA-high) does not express (e.g., expression level is not detectable by the cell state classifier), and no output molecule is produced by the cell state classifier. In some embodiments, the first microRNAs (microRNA low) expresses (e.g., expression level is detectable by the cell state classifier), and the second microRNA (microRNA-high) does not express (e.g., expression level is not detectable by the cell state classifier), and no output molecule or very low output molecule is produced by the cell state classifier. In some embodiments, the first microRNA (microRNA low) expresses (e.g., expression level is detectable by the cell state classifier) or has high expression level, and the second microRNA expresses or has high expression level, and no output molecule or very low output molecule is produced by the cell state classifier.

By placing the target sites for the first or second microRNA (microRNA-low or microRNA-high) in different circuits of the cell state classifier, additional functions of the cell state classifiers can be provided. For example, if the first sensor circuit comprises target sites for the second microRNA (miRNA-high) and the second sensor circuit comprising target sites for the first microRNA (miRNA-low), then the output of the cell state classifier circuit would be reversed such that output would be produced only in cells in which miRNA-low, but not miRNA-high, is expressed.

In some embodiments, to classify the cell, the method further comprises detecting an output molecule produced by the cell state classifier. For example, the output molecule may be fluorescent protein or an enzyme that acts on a substrate. One skilled in the art is familiar with methods of detecting different detectable molecules.

Applications

The cell state classifier described herein may be used for a variety of applications. In some embodiments, the cell state classifier is used for diagnostic purposes. For example, in some embodiments, the cell state classifier may be designed to detect the microRNA profile in a diseased cell (e.g., a cancer cell). As such, if an output signal is detected when such cell state classifier is delivered to a cell, the cell may be classified as a diseased cell (e.g., a cancer cell). For diagnostic purposes, the output molecules of the cell state classifier (e.g., the first or second cell state classifier) is typically a detectable molecule (e.g., a fluorescent protein or chemiluminescent protein). Depending on the cell type to be detected and the specific microRNA profile, in some embodiments, the expression of the first and/or second output molecule indicates a diseased cell. In some embodiments, the lack of expression of the output molecule indicates a diseased cell.

In another example, the cell state classifier is used for therapeutic purposes. For example, in some embodiments, the cell state classifier is designed to detect the microRNA profile in a diseased cell (e.g., a cancer cell) and to produce an output molecule that is a therapeutic molecule (e.g., a therapeutic protein or RNA). Upon detecting of a matching microRNA profile in the diseased cell, the cell state classifier produces the therapeutic molecule, thus treating the disease. Such therapeutic methods are highly specific to the diseased cell and have low impact on healthy cells because the cell state classifier will not detect a matching microRNA profile in a healthy and thus will not produce the output molecule. Further, the therapeutic effect of the cell state classifier is long lasting. For example, the cell state classifier will continuing to produce the therapeutic molecule until the diseased cell no longer has a matching microRNA profile that fit the disease (e.g., cancer). Once therapeutic effects have taken place, the cell state classifier can sense the change in the microRNA profile (e.g., from cancer profile to normal profile) and stop the production of the therapeutic molecule.

For either diagnostic or treatment purposes, the cell may be in vitro (e.g., cultured cell), ex vivo (e.g., isolated from a subject), or in vivo in a subject. For in vivo applications, in some embodiments, the method comprises administering an effective amount of a composition comprising the cell state classifier described herein to a subject in need thereof. The composition can further comprise additional agents (e.g. for specific delivery, increasing half-life, or other therapeutic agents). In some embodiments, the composition further comprises a pharmaceutically acceptable carrier. The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. A "pharmaceutically acceptable carrier" is a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

Some examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22)

bulking agents, such as peptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient," "carrier," "pharmaceutically acceptable carrier" or the like are used interchangeably herein.

An "effective amount" refers to the amount of the cell state classifier or composition comprising such required to confer therapeutic effect on the subject, either alone or in combination with one or more other therapeutic agents. Effective amounts vary, as recognized by those skilled in the art, depending on the particular condition being treated, the severity of the condition, the individual subject parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a subject may insist upon a lower dose or tolerable dose for medical reasons, psychological reasons or for virtually any other reasons.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a disorder. Alternatively, sustained continuous release formulations of agent may be appropriate. Various formulations and devices for achieving sustained release are known in the art.

An effective amount of the cell state classifier or composition comprising such may be administered repeatedly to a subject (e.g., 2, 3, 4, 5, 6, 7, 8, 9, 10 times or more). In some embodiments, dosage is daily, every other day, every three days, every four days, every five days, or every six days. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the agents used) can vary over time.

In some embodiments, for an adult subject of normal weight, doses ranging from about 0.01 to 1000 mg/kg may be administered. In some embodiments, the dose is between 1 to 200 mg. The particular dosage regimen, i.e., dose, timing and repetition, will depend on the particular subject and that subject's medical history, as well as the properties of the agent (such as the half-life of the agent, and other considerations well known in the art).

For the purpose of the present disclosure, the appropriate dosage of the cell state classifiers compositions as described herein will depend on the specific agent (or compositions thereof) employed, the formulation and route of administration, the type and severity of the disorder, previous therapy, the subject's clinical history and response to the agents, and the discretion of the attending physician. Typically the clinician will administer an agent until a dosage is reached that achieves the desired result. Administration can be continuous or intermittent, depending, for example, upon the recipient's physiological condition, and other factors known to skilled practitioners. The administration of an agent may be essentially continuous over a preselected period of time or may be in a series of spaced dose, e.g., either before, during, or after developing a disorder.

A "subject" refers to human and non-human animals, such as apes, monkeys, horses, cattle, sheep, goats, dogs, cats, rabbits, guinea pigs, rats, and mice. In one embodiment, the subject is human. In some embodiments, the subject is an experimental animal or animal substitute as a disease model. A "subject in need thereof" refers to a subject who has or is at risk of a disease or disorder (e.g., cancer).

The cell state classifiers of the present disclosure may be delivered to a subject (e.g., a mammalian subject, such as a human subject) by any in vivo delivery method known in the art. For example, engineered nucleic acids may be delivered intravenously. In some embodiments, engineered nucleic acids are delivered in a delivery vehicle (e.g., non-liposomal nanoparticle or liposome). In some embodiments, the cell state classifiers are delivered systemically to a subject having a cancer or other disease and produces a therapeutic molecule specifically in cancer cells or diseased cells of the subject. In some embodiments, the cell state classifiers are delivered to a site of the disease or disorder (e.g., site of cancer).

Non-limiting examples of cancers that may be treated using the cell state classifiers and methods described herein include: premalignant neoplasms, malignant tumors, metastases, or any disease or disorder characterized by uncontrolled cell growth such that it would be considered cancerous or precancerous. The cancer may be a primary or metastatic cancer. Cancers include, but are not limited to, ocular cancer, biliary tract cancer, bladder cancer, pleura cancer, stomach cancer, ovary cancer, meninges cancer, kidney cancer, brain cancer including glioblastomas and medulloblastomas, breast cancer, cervical cancer, choriocarcinoma, colon cancer, endometrial cancer, esophageal cancer, gastric cancer, hematological neoplasms including acute lymphocytic and myelogenous leukemia, multiple myeloma, AIDS-associated leukemias and adult T-cell leukemia lymphoma, intraepithelial neoplasms including Bowen's disease and Paget's disease, liver cancer, lung cancer, lymphomas including Hodgkin's disease and lymphocytic lymphomas, neuroblastomas, oral cancer including squamous cell carcinoma, ovarian cancer including those arising from epithelial cells, stromal cells, germ cells and mesenchymal cells, pancreatic cancer, prostate cancer, rectal cancer, sarcomas including leiomyosarcoma, rhabdomyosarcoma, liposarcoma, fibrosarcoma, and osteosarcoma, skin cancer including melanoma, Kaposi's sarcoma, basocellular cancer, and squamous cell cancer, testicular cancer including germinal tumors such as seminoma, non-seminoma, teratomas, choriocarcinomas, stromal tumors and germ cell tumors, thyroid cancer including thyroid adenocarcinoma and medullar carcinoma, and renal cancer including adenocarcinoma and Wilms' tumor. Commonly encountered cancers include breast, prostate, lung, ovarian, colorectal, and brain cancer. In some embodiments, the tumor is a melanoma, carcinoma, sarcoma, or lymphoma.

EXAMPLES

Example 1: A miRNA Sensor that Alters Transcription Factor Phosphorylation State Introduction Sensing cellular biomarkers enables the identification of unique cell types in a complex mixture of cells, such as a tissue. With cell-type classifiers, "smart" therapeutics which encode cell-type specific cellular outcomes, such as the selective killing cancer cells, can be created[1]. microRNAs (miRNAs) are a compelling biomarker to use in cell classifiers because there are hundreds of known miRNAs that are differentially expressed in each cell type. miRNA sensors work by driving high output expression when certain miRNAs in the cell are at low (low-miRs) or high (high-miRs) concentrations (Table 5). Low-miR sensors are simple, consisting of an output protein with miRNA target sites placed in its untranslated region(s). The state of the art high-miR sensor is more complex: miRNA target sites are placed in the untranslated region(s) of a transcriptional repressor protein, which blocks transcription of the classifier output[1]. Thus, when high-miRs are indeed at high concentrations, the repressor concentration is knocked down such that output can be transcribed. A race condition exists when the high-miR is low or absent, affecting the performance of the miR-high sensor: the output may be expressed before enough repressor can be produced to stop the initial transcriptional burst. To resolve this condition, delay mechanism was introduced in more recent designs, but balancing the race condition and repression versus activation strength remains a confounding factor for design. Herein a novel miRNA sensor design, which utilizes phosphorylation of a transcription factor to control classifier output, is described (FIG. 1). With this design, the race condition is eliminated, and the tuning of repressor/activator strength is easier since there is no need to develop a hybrid promoter with non-linear input-output activity.

TABLE 5 miRNA Classifier Truth Table. The output of a miRNA sensor should only be high ("on") when the low-miRs are at low concentrations/absent, and the high-miRs are at high concentrations.

| Low-miR(s) | High-miR(s) | Output |
| --- | --- | --- |
| 0 | 0 | 0 |
| 0 | 1 | 1 |
| 1 | 0 | 0 |
| 1 | 1 | 0 |

Design:

As shown in FIG. 1, the new miRNA classifier is based on phosphorylation of a transcriptional activator (TF). The phosphorylation of the TF (TF-P) causes a conformational change that enables or abrogates DNA binding (in this implementation, phosphorylation enables DNA binding). A kinase (K) and a phosphatase (P) are constitutively expressed from separate transcription units (TUs). K and TF are expressed from the same TU and have low-miR target sites in their untranslated regions (UTRs). This ensures that the presence of low-miR(s) represses activation of the TF-driven promoter. The TF-driven promoter directly produces the circuit output, which also has low-miR target sites in its UTRs. This further helps to suppress output when the low-miR(s) are present. P has high-miR target sites in its UTRs such that the presence of high-miR(s) represses the negative phosphorylation reaction, allowing TF to remain phosphorylated by K and to activate output expression. In the absence of any miRNA inputs, the phosphatase should dominate the interaction with TF, causing TF-P to be limiting and the output to not be expressed.

Selection of Kinases, Phosphatases, and Transcription Factors

K, P, and TF were all derived from *E. coli* two-component signaling (TCS) components and modified for use in mammalian cells. TCS systems are characterized by pairs of transmembrane histidine kinases (HKs) and cytoplasmic response regulators (RRs). Typically, upon extracellular signal induction, the HK will auto-phosphorylate a conserved histidine residue in the dimerization and histidine phosphorylation (DHp) domain of the protein. The phosphate group is then rapidly transferred to the HK's cognate RR protein on a conserved aspartate residue in the receiver domain of the protein. This phosphate group causes a conformational change in the RR. Many RRs are TFs, and their binding to DNA is controlled by this conformational change. A critical feature of many HKs is that in the absence of signal input, they act as a phosphatase on their cognate RR, ensuring low output in the absence of input. There are over 30 HK-RR pairs in *E. coli* alone and most act orthogonally, making the creation of a large library of orthogonally acting kinases, phosphatases, and transcription factor targets feasible. In addition, some HKs and RRs have been shown to function in mammalian cells[2]. However, the HKs investigated were shown to be constitutively active and unresponsive to extracellular signal input[2].

To create individual K and P proteins, variants of several HK proteins were generated to isolate their native kinase and phosphatase functions. Research in bacteria and in vitro showed that the kinase and phosphatase functions of HKs are independently and necessarily dependent on two conserved residues immediately downstream of the phosphohistidine[3]. Most HKs have a conserved core called an H-box within their DHp domain surrounding the phosphohistidine. Within the H-box is a highly-conserved stretch of amino acids that roughly adheres to one of these patterns: HpEXXN, HpEXXT, and HpDXXXP, where Hp is the phosphohistidine, E is glutamate, D is aspartate, N is asparagine, P is proline, and X is any residue. To generate P proteins, the E/D residue was mutated to an alanine, eliminating auto-phosphorylation and phosphorylation of the cognate RR[3]. To generate K proteins, the N/P residue was mutated to an alanine, eliminating phosphorylation activity[3]. This was the first time that these mutations have been shown to also be effective in creating kinase- and phosphatase-null proteins in mammalian cells, and that these variants can differentially regulate their target RR to >400-fold changes in RR-driven promoter activity as measured by flow cytometry (see Results). The first set of TCS proteins tested and described herein include EnvZ-OmpR, NarX-NarL, NtrB-NtrC, and PhoR-PhoB.

Output Promoter Design

OmpR-, NarL-, NtrC-, and PhoB-driven promoters were designed by placing 1, 2, or 3 response elements (REs) upstream of a minimal CMV promoter or a minimal TATA box designed by the Benenson Lab[2]. Response elements were separated by 12 bp cloning scars and each contain 3 TF operators each spaced with a 5 bp (DNA half-turn) spacer. OmpR operator: ATTTACATTTTGAAACATCTA (SEQ ID NO: 28)[4]. NarL operator: TACCGCTATTGAGGTA (SEQ ID NO: 29)[5]. NtrC operator: TGCACTAAAATGGTGCA (SEQ ID NO: 30)[6]. PhoB operator: CTGTCAT-AWAWCTGTCAY (SEQ ID NO: 31) (W=A/T, Y=C/T)[7]. For PhoB, nucleotides were randomly selected for the ambiguous sequences such that each operator within an RE was different.

The creation of several different promoter variants allow for the selection of minimal and maximal output that is desired from the miRNA sensor.

Placement and Number of miRNA Target Sites miR target sites were placed in tandem groups of 4 in both the 3' and 5' UTR of target proteins to ensure maximum knockdown.

Balancing Kinase and Phosphatase Strengths

For each K/P pair derived from an HK protein, experimental transfection titrations were performed to identify the maximum level of K that can be expressed given some concentration of P such that output is not increased above levels seen in the absence of K. At these relative levels, it can be ensured that output expression is low in the absence of any miRNA, and the presence of miRNA against the P will cause the K to dominate, phosphorylate the RR, and drive output expression.

Results:

Derivation of Kinase and Phosphatase Proteins

Figure 2:
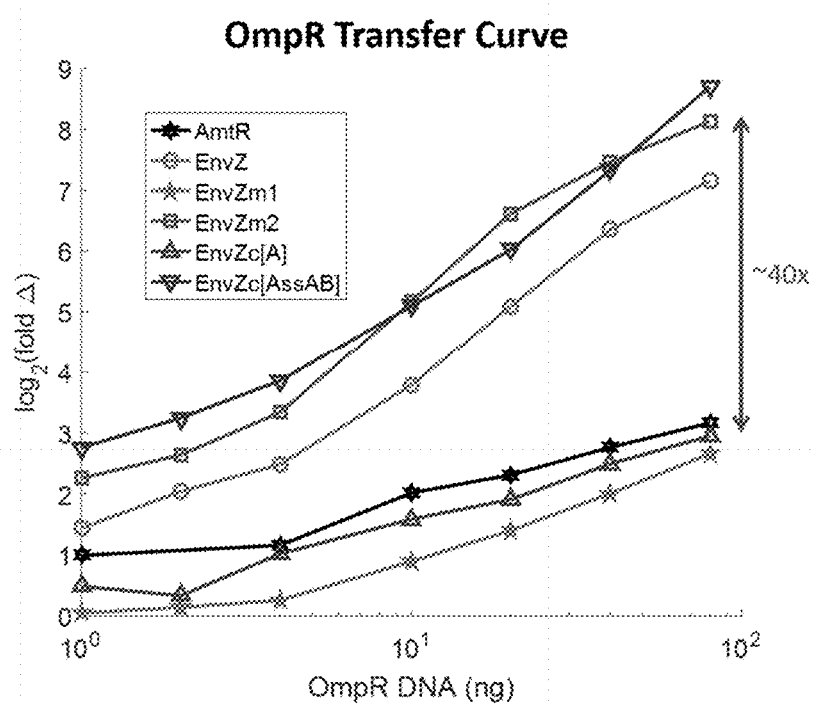
FIG. 2: Comparing EnvZ Variants. OmpR-VP64 was titrated in the presence of different EnvZ variants. The upper three lines indicate a predicted kinase and the lower three lines indicate a predicted phosphatase. AmtR is an unreactive transcription factor used as an inert control input to see basal activity. OmpR-driven mKate2 median fluorescent out-put was measured and the fold-change between each level of OmpR and 0 ng OmpR were calculated.

The EnvZ histidine kinase protein coding sequence was obtained by gBlock from IDT. The sequence was cloned into a Level 0 vector[8] and was modified with PCR to generate variants EnvZm1 (D244A), EnvZm2 (T247A), EnvZc[A] (DHp domain only[9]), and EnvZc[AssAB] (an extra DHp domain fused to the cytoplasmic portion of EnvZ[10]). These variants and WT EnvZ were all cloned after the hEF1a promoter. The variants were all transfected into HEK-293FT cells with a titration of OmpR fused to the VP64 activation domain in order to identify the OmpR transfer curve in the presence of each variant. OmpR activated a promoter driving mKate2 output (6xmCMV37, see FIG. 3). mKate2 median fluorescence output was measured and the fold-change between each level of OmpR and 0 ng OmpR input were compared (FIG. 2). The TetR homolog transcription factor AmtR was used as a control protein with no interaction with the EnvZ-OmpR system. A 40-fold change between the EnvZm1 and EnvZm2 driven outputs at the highest levels of OmpR was observed.

Promoter Strength Measurements

Figure 3:
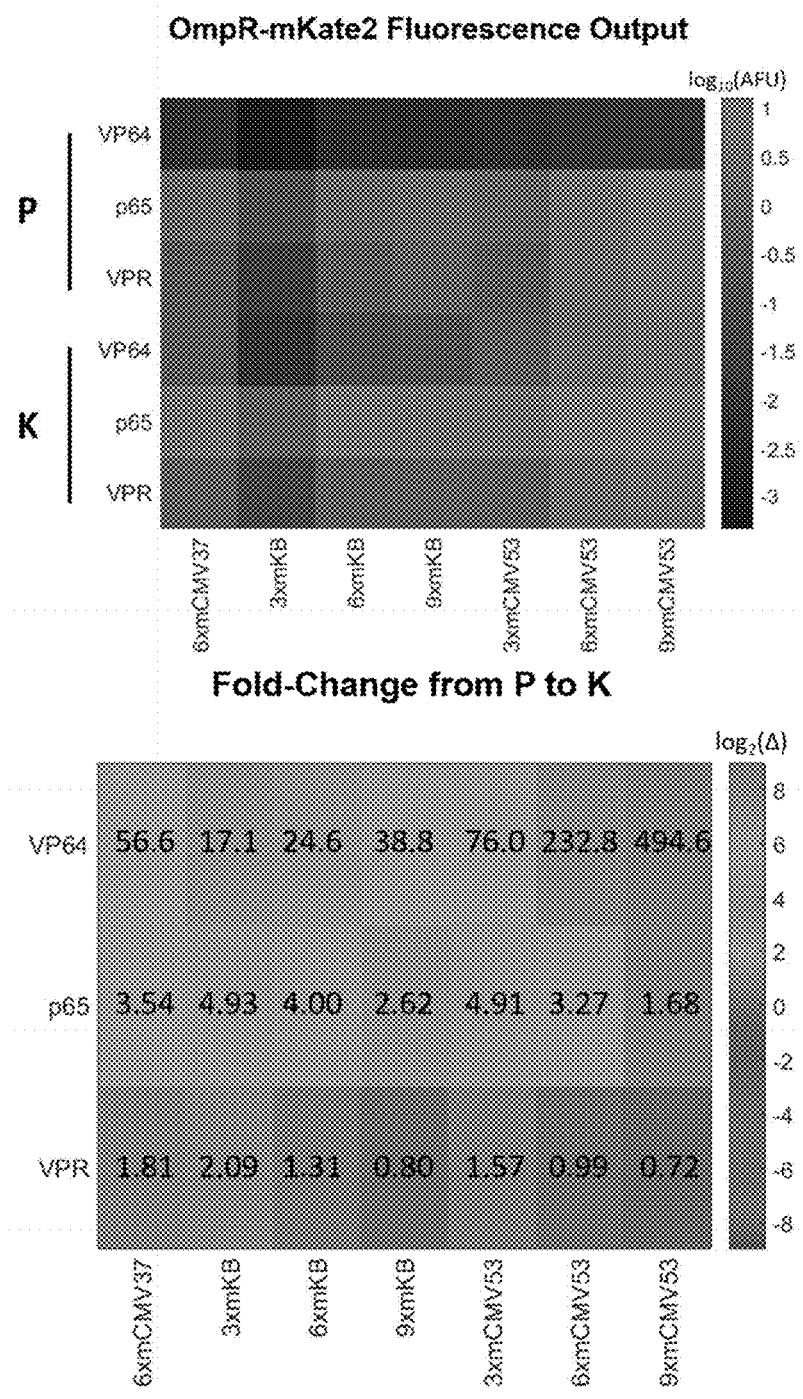
FIG. 3: OmpR Promoters Comparison. OmpR promoters with 3, 6, and 9 OmpR binding sites and different minimal promoters were compared for mKate2 fluorescent output, which is shown in the heat map in the top panel. The promoter output was measured in the presence of either a kinase or phosphatase variant of EnvZ (K, P). The fold-change between the output in the presence of the kinase or phosphatase was recorded and shown in the heatmap in the bottom panel.

Promoters with 3, 6, or 9 OmpR binding sites upstream of either a minimal CMV promoter or a minimal promoter developed by the Benenson Laboratory were built[2]. The promoters were cloned upstream of the mKate2 red fluorescent protein, and transfected into HEK-293FT cells in the presence of the EnvZm1 (phosphatase) or EnvZm2 (kinase) variants and OmpR fused to different activation domains: VP64, p65 (NF-kB), and VPR[11]. The median fluorescence output for each sample was measured and the fold-change between samples was calculated with the same promoter when the kinase or phosphatase was present (FIG. 3). An almost 500-fold change in activity was observed for the strongest promoter when using OmpR-VP64. Though the stronger promoters had better fold-changes, the weaker promoters may be better for classifiers due to less basal expression.

Relative Kinase and Phosphatase Strengths

To compare the relative strengths of EnvZ kinases and phosphatases, HEK-293FT cells were transfected with EnvZm2 and a titration of EnvZm2 or EnvZ[AssAB] inputs, OmpR-VP64, and OmpR-driven mKate2 (FIG. 4). mKate2 median fluorescent output was compared for three different scenarios: (1) Open-loop, where there was no phosphatase, (2) Feedback, where the phosphatase was co-expressed with mKate2, and (3) Const. P, where 30 ng of constitutively expressed EnvZm2 phosphatase was expressed. Since the kinase and phosphatases have the same promoters and are roughly the same size, it can be assumed that at equal plasmid input levels, the amount of protein produced is roughly equivalent. When the kinase and phosphatase are balanced in concentration and strength or favor the kinase, the mKate2 output will be maximized. The plots show that EnvZ[AssAB] is ~3× stronger than EnvZm1, and that EnvZm2 is <3× stronger (since the Const. P does not recover to Open-loop levels in the titration range).

Figure 4:
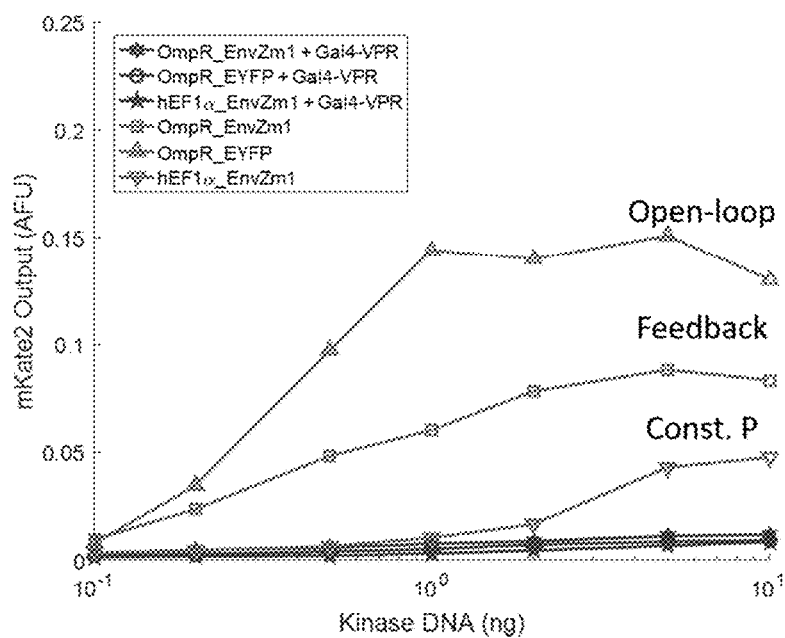
FIG. 4: Relative K and P Activity. The EnvZm2 (top) and EnvZ[AssAB] (bottom) variants were titrated in with constant levels of OmpR-VP64 and OmpR-driven mKate2. The kinase titrations alone (open-loop, Δ), with an OmpR-activated promoter driving both mKate2 and EnvZm1 phosphatase (feedback, □), and with 30 ng constitutively expressed EnvZm1 (Const. P, ∇) were tested.
Figure 4:
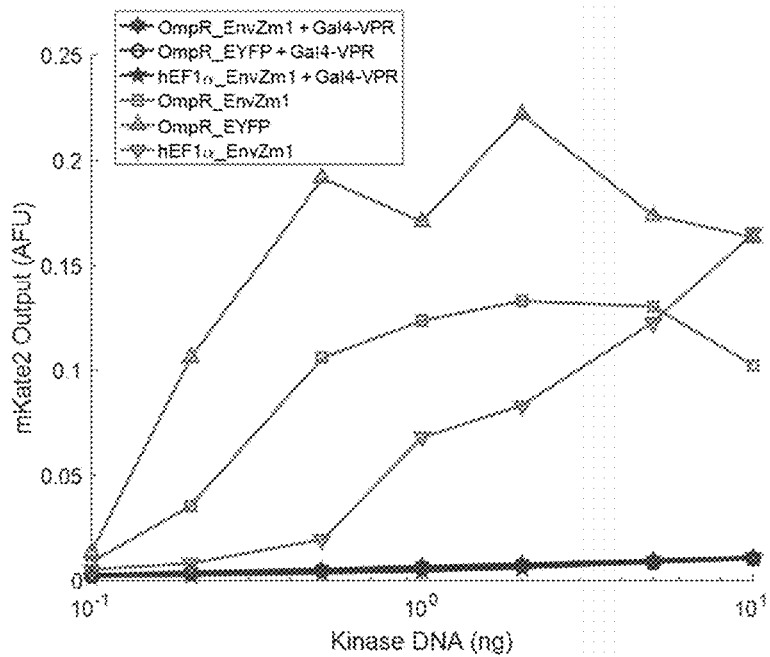

These results can be used to select optimal kinase and phosphatase expression levels for the classifier. When there is no miRNA input, the phosphatase should dominate the kinase and suppress output. When the high miRNA is present, the phosphatase should be repressed enough such that the kinase can dominate and drive high output. Thus, kinase levels to maximize the difference in fluorescence output between the Open-loop and Const. P conditions need to be selected. FIG. 4 shows that this difference is maximized by using the EnvZm2 kinase with <1 ng input. EnvZ[AssAB] also showed strong fold-changes between the Open-loop and Const. P conditions, but was more sensitive to low levels of kinase, potentially making a classifier using it instead of EnvZm2 more likely to fail.

miRNA Sensor Activity

Figure 5:
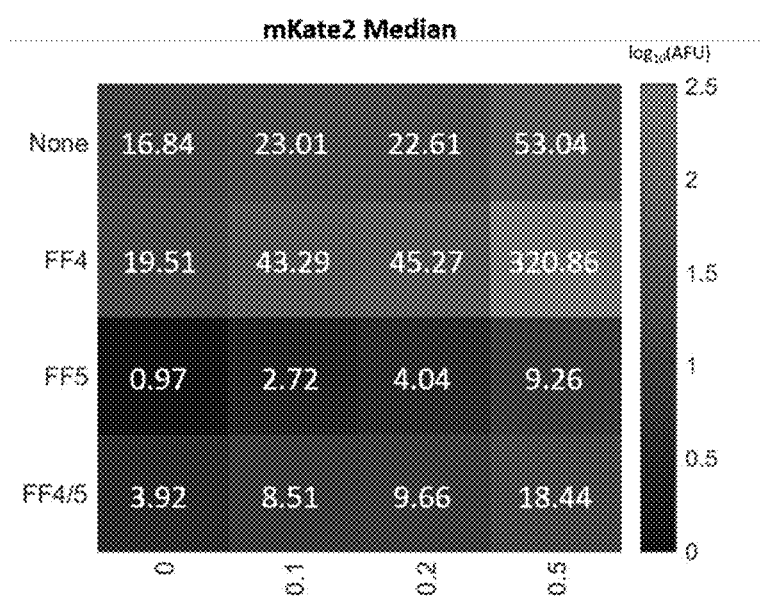
FIG. 5: Classifier Function. HEK-293FT cells were transfected with the full classifier circuit in the presence of different miRNA input combinations and varying kinase input levels (columns, ng EnvZm2). FF4 is the high-miR input, FF5 is the low-miR input. Classifier output mKate2 median fluorescence output is shown in the heatmap. The classifier should be "on" when FF4 is high and "off" otherwise.

Preliminary results for classifier activity were collected by transfecting HEK-293FT cells with EnvZm1 phosphatase, OmpR-VP64, OmpR-driven mKate2, varying input levels of EnvZm2 kinase, and all combinations of the synthetic miR-NAs FF4 and FF5. Four FF4 and FF5 target sites were placed in tandem in the 3'UTRs of the kinase, phosphatase, OmpR, and mKate2 as shown in FIG. 1 to fully implement the controller. FF4 and FF5 were expressed from a miR-155 template from the Zhen Laboratory[12]. mKate2 median fluorescence output values were measured and compared at each kinase input level to test the classifier function (FIG. 5). At 0.5 ng EnvZm2 input, a 6-fold change in sensing FF4 compared to no miRNA, and higher fold changes compared to the other input combinations, was observed. This preliminary data demonstrates the ability to selectively drive output expression in the presence of a high-miR (FF4).

Methods:

HEK-293FT Culture and Transfection

HEK-293FT cells were grown in Dulbecco's modification of Eagle's minimal essential media (DMEM, Corning) with 10% FBS (VWR). Cells were cultured to 90% confluency on the day of transfection, and were plated out simultaneously with the addition of transfection reagents. Transfections were performed in 96-well pre-treated culture plates (Costar). Up to 150 ng total DNA were pre-diluted in 10 μL Opti-MEM (Thermo Fisher) before adding Viafect transfection reagent (Promega) in a ratio of 3 μL Viafect per 1 ug DNA. The DNA-Viafect mixture were incubated for 10-20 minutes while cells were trypsinized and counted. After depositing the transfection mixture into appropriate wells, 30,000 cells in 100 μL media were added.

Flow Cytometry

Fluorescence output was measured 48 hours after transfection using the LSR-II Fortessa Flow Cytometer in the Synthetic Biology Center at the Massachusetts Institute of Technology.

For each well of the 96-well plate, the media is aspirated, 50 μL PBS (Corning) was added to wash the cells, and 40 μL Trypsin-EDTA (Corning) is added. The cells were allowed to detach for 5-10 minutes at 37° C. Following incubation, 80 μL of DMEM without phenol red (Invitrogen) with 10% FBS was added to the trypsinized cells and were thoroughly mixed to separate and suspend individual cells. The plate was spun down at 400 g for 4 minutes, and the leftover media was aspirated. Cells were resuspended in 80-110 μL of PBS supplemented with 1% BSA (Thermo Fisher), 5 mM EDTA (VWR), and 0.1% sodium azide (Sigma-Aldrich) to prevent clumping.

The plate was run on the HTS attached to the Fortessa using the following parameters: 2.0-2.5 µL/sec flow speed. 60-80 µL flow volume, 40-60 µL mixing volume, 250 µL/sec mixing speed, 400 µL wash volume.

Flow Cytometry Data Analysis

Single cells were isolated by drawing gates based on cellular side-scatter and forward-scatter. Transfected cells were isolated by drawing a gate on TagBFP fluorescence in the Pacific Blue Area channel. The median fluorescence of mKate2 output was calculated on this gate in the PE-Texas Red Area channel. mKate2 median fluorescence was used to determine classifier output given different miRNA inputs.

CONCLUSIONS

Herein miRNA-based cell-type classifiers that use phosphorylation state of a transcription factor to control output expression are described. Kinases, phosphatases, and cognate transcription factors can be transferred from E. coli to human cells and mutated to alter functionality. Optimal promoter strengths can be derived by altering the number of promoter binding sites. Relative kinase and phosphatase levels can be optimized to maximize the fold-change in kinase-driven output in the presence and absence of phosphatase. All this information can be combined to build a functioning miRNA classifier with >6-fold difference in activity between matching and non-matching miRNA profiles.

REFERENCES

1. Xie, Z., Wroblewska, L., Prochazka, L., Weiss, R., and Benenson, Y. (2011) Multi-Input RNAi-Based Logic Circuit for Identification of Specific Cancer Cells. *Science* (80-.). 333, 1307-1311.
2. Hansen, J., Mailand, E., Swaminathan, K. K., Schreiber, J., Angelici, B., and Benenson, Y. (2014) Transplantation of prokaryotic two-component signaling pathways into mammalian cells. *PNAS* 111, 15705-15710.
3. Willett, J. W., and Kirby, J. R. (2012) Genetic and Biochemical Dissection of a HisKA Domain Identifies Residues Required Exclusively for Kinase and Phosphatase Activities. *PLoS Genet.* 8, e1003084.
4. Mizuno, T., Kato, M., Jo, Y.-L., and Mizushima, S. (1988) Interaction of OmpR, a positive regulator, with the osmoregulated ompC and ompF genes of *Escherichia coli*. Studies with wild-type and mutant OmpR proteins. *J. Biol. Chem.* 263, 1008-1012.
5. Li, J., and Stewart, V. (1992) Localization of upstream sequence elements required for nitrate and anaerobic induction of fdn (formate dehydrogenase-N) operon expression in *Escherichia coli* K-12. *J. Bacteriol.* 174, 4935-4942.
6. Porter, S. C., North, A. K., Wedel, A. B., and Kustu, S. (1993) Oligomerization of NTRC at the glnA enhancer is required for transcriptional activation. *Genes Dev.* 7, 2258-2273.
7. Makino, K., Amemura, M., Kawamoto, T., Kimura, S., Shinagawa, H., Nakata, A., and Suzuki, M. (1996) DNA binding of PhoB and its interaction with RNA polymerase. *J. Mol. Biol.* 259, 15-26.
8. Duportet, X., Wroblewska, L., Guye, P., Li, Y., Eyquem, J., Rieders, J., Rimchala, T., Batt, G., and Weiss, R. (2014) A platform for rapid prototyping of synthetic gene networks in mammalian cells. *Nucleic Acids Res.* 42, 13440-13451.
9. Zhu, Y., Qin, L., Yoshida, T., and Inouye, M. (2000) Phosphatase activity of histidine kinase EnvZ without kinase catalytic domain. *PNAS* 97, 7808-7813.
10. Qin, L., Dutta, R., Kurokawa, H., Ikura, M., and Inouye, M. (2000) A monomeric histidine kinase derived from EnvZ, an *Escherichia coli* osmosensor. *Mol. Microbiol.* 36, 24-32.
11. Chavez, A., Scheiman, J., Vora, S., Pruitt, B. W., Tuttle, M., P R Iyer, E., Lin, S., Kiani, S., Guzman, C. D., Wiegand, D. J., Ter-Ovanesyan, D., Braff, J. L., Davidsohn, N., Housden, B. E., Perrimon, N., Weiss, R., Aach, J., Collins, J. J., and Church, G. M. (2015) Highly efficient Cas9-mediated transcriptional programming. *Nat. Methods* 12, 326-328.
12. Wang, T., Xie, Y., Tan, A., Li, S., and Xie, Z. (2015) Construction and characterization of synthetic microRNA cluster for multiplex RNA interference in mammalian cells. *ACS Synth. Biol.* 565, acssynbio.5b00180.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A cell state classifier, comprising:

(i) a first sensor circuit comprising a constitutive promoter operably linked to a nucleotide sequence encoding an activator, and a constitutive promoter operably linked to a nucleotide sequence encoding a kinase that phosphorylates the activator and produces a phosphorylated activator, and one or more target sites for a first microRNA;

(ii) a second sensor circuit comprising a constitutive promoter operably linked to a nucleotide sequence encoding a phosphatase that de-phosphorylates the phosphorylated activator, and one or more target sites for a second microRNA; and (iii) a signal circuit comprising an activatable promoter that is activated by the phosphorylated activator, operably linked to a nucleotide sequence encoding an output molecule, and one or more target sites for the first microRNA, optionally wherein the constitutive promoter of (i) and the constitutive promoter of (ii) are the same or wherein the constitutive promoter of (i) and the constitutive promoter of (ii) are different, wherein the kinase, the phosphatase, and/or the activator are members of a bacterial two-component signaling system, wherein the bacterial two-component system comprises a histidine kinase comprising an amino acid sequence motif of HEXXN, HEXXT, or HDXXXP, wherein X is any amino acid, and a response regulator, and wherein the phosphatase is a variant of the histidine kinase and comprises an amino acid substitution in the E or D of the HEXXN, HEXXT or HDXXXP motif.

2. The cell state classifier of claim 1, wherein the kinase is a variant of the histidine kinase and comprises an amino acid substitution in the N, T, or P of the HEXXN, HEXXT or HDXXXP motif, optionally wherein the kinase comprises an alanine substitution in the N, T, or P of the HEXXN, HEXXT, or HDXXXP motif.

3. The cell state classifier of claim 2, wherein the histidine kinase is selected from the group consisting of: EnvZ, NarX, and PhoR, optionally wherein the histidine kinase comprises the amino acid sequence of SEQ ID NO: 1, optionally wherein the phosphatase comprises an amino acid substitution corresponding to a D244A substitution in SEQ ID NO: 1, optionally wherein the phosphatase comprises the amino acid sequence of SEQ ID NO:2;

optionally wherein the histidine kinase comprises an amino acid substitution corresponding to a T247A substitution in SEQ ID NO: 1, optionally wherein the histidine kinase comprises the amino acid sequence of SEQ ID NO: 3;
optionally wherein the phosphatase comprises a dimerization and histidine phosphorylation (DHp) domain of EnvZ, optionally wherein the phosphatase comprises the amino acid sequence of SEQ ID NO: 4 or wherein the histidine kinase comprises two DHp domains fused to a cytoplasmic domain of EnvZ, optionally wherein the histidine kinase comprises the amino acid sequence of SEQ ID NO: 5.

4. The cell state classifier of claim 2, wherein the activator comprises the response regulator of the bacterial two-component system; or wherein the activator comprises the response regulator of the bacterial two-component system fused to an activation domain, optionally wherein the activation domain is selected from the group consisting of: VP16, VP64, p65, and VPR; and/or
wherein the activation domain is selected from the group consisting of: VP16, VP64, p65, and VPR;
optionally wherein the response regulator is selected from the group consisting of: OmpR, NarL, NtrC, and PhoB.

5. The cell state classifier of claim 1, wherein the phosphatase is a variant of the histidine kinase and comprises an alanine substitution in the E or D of the HEXXN, HEXXT, or HDXXXP motif.

6. The cell state classifier of claim 1, wherein the activatable promoter comprises one or more response elements that binds to the activator;
optionally wherein the response element comprises one or more operators of the activator;
optionally wherein the activatable promoter further comprises a minimal promoter fused to the one or more response elements.

7. The cell state classifier of claim 1, wherein the one or more target sites for the first microRNA is located upstream and/or downstream of the nucleotide sequence encoding the activator and the nucleotide sequence encoding the kinase in the first sensor circuit, optionally wherein 4 target sites for the first microRNA are located upstream and/or downstream of the nucleotide sequence encoding the activator and the nucleotide sequence encoding the kinase in the first sensor circuit; and/or
wherein the one or more target sites for the first microRNA is located upstream and/or downstream of the nucleotide sequence encoding the output molecule in the signal circuit; and/or
wherein 4 target sites for the first microRNA are located upstream and/or downstream of the nucleotide sequence encoding the output molecule in the signal circuit; and/or
wherein the one or more target sites for the second microRNA is located upstream and/or downstream of the nucleotide sequence encoding the phosphatase in the second sensor circuit, optionally wherein 4 target sites for the second microRNA are located upstream and/or downstream of the nucleotide sequence encoding the phosphatase in the second sensor circuit.

8. The cell state classifier of claim 1, wherein the output molecule is a detectable molecule or a therapeutic molecule.

9. A method comprising delivering the cell state classifier of claim 1 to an in vitro or ex vivo cell and detecting an output molecule.

10. A method of treating a disease or disorder comprising delivering the cell state classifier of claim 1 to a cell, wherein the output molecule is a therapeutic molecule that is effective for treating the disease or disorder,
optionally wherein the cell is a diseased cell, or optionally wherein the cell is a cancer cell.

11. A method of diagnosing a disease or disorder comprising delivering the cell state classifier of claim 1 to an in vitro or ex vivo cell,
optionally wherein the cell is a diseased cell, or optionally wherein the cell is a cancer cell.

12. The method of claim 11, the method further comprising detecting the output molecule,
optionally wherein the expression of the output molecule indicates the disease or disorder, or
optionally wherein the lack of expression of the output molecule indicates the disease or disorder.

13. A method of treating a disease or disorder, the method comprising administering an effective amount of a composition comprising the cell state classifier of claim 1 to a subject in need thereof, wherein the output molecule is a therapeutic molecule that is effective for treating the disease or disorder, optionally wherein the composition further comprises a pharmaceutically acceptable carrier.

14. A method of diagnosing a disease or disorder comprising administering an effective amount of a composition comprising the cell state classifier of claim 1 to in vitro or ex vivo cells of a subject in need thereof, and detecting the output molecule, optionally wherein the composition further comprises a pharmaceutically acceptable carrier.

15. An isolated cell comprising the cell state classifier of claim 1;
optionally wherein the cell is a prokaryotic cell, optionally a bacterial cell;
optionally wherein the cell is a eukaryotic cell, optionally a plant cell, an insect cell, or a mammalian cell, optionally a human cell.

16. The isolated cell of claim 15, wherein the cell is a diseased cell, optionally a cancer cell.

17. The isolated cell of claim 15, wherein the cell does not express the first microRNA; and/or
wherein the cell expresses the second microRNA; and/or
wherein the cell expresses the first microRNA and does not express the second microRNA; and/or
wherein the cell expresses the first microRNA and expresses the second microRNA; and/or
wherein the cell does not express the first microRNA and does not express the second microRNA.

18. A method comprising maintaining the cell of claim 15 in vitro or ex vivo, optionally further comprising detecting the output molecule, or optionally further comprising classifying the cell.

* * * * *

SEQUENCE LISTING

```
Sequence total quantity: 31
SEQ ID NO: 1            moltype = AA  length = 450
FEATURE                 Location/Qualifiers
source                  1..450
                        mol_type = protein
                        organism = Escherichia coli
SEQUENCE: 1
```

```
MRRLRFSPRS SFARTLLLIV TLLFASLVTT YLVVLNFAIL PSLQQFNKVL AYEVRMLMTD    60
KLQLEDGTQL VVPPAFRREI YRELGISLYS NEAAEEAGLR WAQHYEFLSH QMAQQLGGPT   120
EVRVEVNKSS PVVWLKTWLS PNIWVRVPLT EIHQGDFSPL FRYTLAIMLL AIGGAWLFIR   180
IQNRPLVDLE HAALQVGKGI IPPPLREYGA SEVRSVTRAF NHMAAGVKQL ADDRTLLMAG   240
VSHDLRTPLT RIRLATEMMS EQDGYLAESI NKDIEECNAI IEQFIDYLRT GQEMPMEMAD   300
LNAVLGEVIA AESGYEREIE TALYPGSIEV KMHPLSIKRA VANMVVNAAR YGNGWIKVSS   360
GTEPNRAWFQ VEDDGPGIAP EQRKHLFQPF VRGDSARTIS GTGLGLAIVQ RIVDNHNGML   420
ELGTSERGGL SIRAWLPVPV TRAQGTTKEG                                    450

SEQ ID NO: 2           moltype = AA  length = 450
FEATURE                Location/Qualifiers
source                 1..450
                       mol_type = protein
                       organism = Escherichia coli
SEQUENCE: 2
MRRLRFSPRS SFARTLLLIV TLLFASLVTT YLVVLNFAIL PSLQQFNKVL AYEVRMLMTD    60
KLQLEDGTQL VVPPAFRREI YRELGISLYS NEAAEEAGLR WAQHYEFLSH QMAQQLGGPT   120
EVRVEVNKSS PVVWLKTWLS PNIWVRVPLT EIHQGDFSPL FRYTLAIMLL AIGGAWLFIR   180
IQNRPLVDLE HAALQVGKGI IPPPLREYGA SEVRSVTRAF NHMAAGVKQL ADDRTLLMAG   240
VSHALRTPLT RIRLATEMMS EQDGYLAESI NKDIEECNAI IEQFIDYLRT GQEMPMEMAD   300
LNAVLGEVIA AESGYEREIE TALYPGSIEV KMHPLSIKRA VANMVVNAAR YGNGWIKVSS   360
GTEPNRAWFQ VEDDGPGIAP EQRKHLFQPF VRGDSARTIS GTGLGLAIVQ RIVDNHNGML   420
ELGTSERGGL SIRAWLPVPV TRAQGTTKEG                                    450

SEQ ID NO: 3           moltype = AA  length = 450
FEATURE                Location/Qualifiers
source                 1..450
                       mol_type = protein
                       organism = Escherichia coli
SEQUENCE: 3
MRRLRFSPRS SFARTLLLIV TLLFASLVTT YLVVLNFAIL PSLQQFNKVL AYEVRMLMTD    60
KLQLEDGTQL VVPPAFRREI YRELGISLYS NEAAEEAGLR WAQHYEFLSH QMAQQLGGPT   120
EVRVEVNKSS PVVWLKTWLS PNIWVRVPLT EIHQGDFSPL FRYTLAIMLL AIGGAWLFIR   180
IQNRPLVDLE HAALQVGKGI IPPPLREYGA SEVRSVTRAF NHMAAGVKQL ADDRTLLMAG   240
VSHDLRAPLT RIRLATEMMS EQDGYLAESI NKDIEECNAI IEQFIDYLRT GQEMPMEMAD   300
LNAVLGEVIA AESGYEREIE TALYPGSIEV KMHPLSIKRA VANMVVNAAR YGNGWIKVSS   360
GTEPNRAWFQ VEDDGPGIAP EQRKHLFQPF VRGDSARTIS GTGLGLAIVQ RIVDNHNGML   420
ELGTSERGGL SIRAWLPVPV TRAQGTTKEG                                    450

SEQ ID NO: 4           moltype = AA  length = 67
FEATURE                Location/Qualifiers
source                 1..67
                       mol_type = protein
                       organism = Escherichia coli
SEQUENCE: 4
MAAGVKQLAD DRTLLMAGVS HDLRAPLTRI RLATEMMSEQ DGYLAESINK DIEECNAIIE    60
QFIDYLR                                                              67

SEQ ID NO: 5           moltype = AA  length = 303
FEATURE                Location/Qualifiers
source                 1..303
                       mol_type = protein
                       organism = Escherichia coli
SEQUENCE: 5
MAAGVKQLAD DRTLLMAGVS HDLRTPLTRI RLATEMMSEQ DGYLAESINK DIEECNAIIE    60
QFIDYLRGGS IGGSIMAAGV KQLADDRTLL MAGVSHDLRT PLTRIRLATE MMSEQDGYLA   120
ESINKDIEEC NAIIEQFIDY LRTGQEMPME MADLNAVLGE VIAAESGYER EIETALYPGS   180
IEVKMHPLSI KRAVANMVVN AARYGNGWIK VSSGTEPNRA WFQVEDDGPG IAPEQRKHLF   240
QPFVRGDSAR TISGTGLGLA IVQRIVDNHN GMLELGTSER GGLSIRAWLP VPVTRAQGTT   300
KEG                                                                 303

SEQ ID NO: 6           moltype = AA  length = 78
FEATURE                Location/Qualifiers
REGION                 1..78
                       note = Synthetic Polypeptide
source                 1..78
                       mol_type = protein
                       organism = synthetic construct
SEQUENCE: 6
APPTDVSLGD ELHLDGEDVA MAHADALDDF DLDMLGDGDS PGPGFTPHDS APYGALDMAD    60
FEFEQMFTDA LGIDEYGG                                                  78

SEQ ID NO: 7           moltype = AA  length = 62
FEATURE                Location/Qualifiers
REGION                 1..62
                       note = Synthetic Polypeptide
source                 1..62
                       mol_type = protein
                       organism = synthetic construct
```

```
SEQUENCE: 7
EASGSGRADA LDDFDLDMLG SDALDDFDLD MLGSDALDDF DLDMLGSDAL DDFDLDMLIN    60
SR                                                                  62

SEQ ID NO: 8            moltype = AA  length = 261
FEATURE                 Location/Qualifiers
REGION                  1..261
                        note = Synthetic Polypeptide
source                  1..261
                        mol_type = protein
                        organism = synthetic construct
SEQUENCE: 8
SQYLPDTDDR HRIEEKRKRT YETFKSIMKK SPFSGPTDPR PPPRRIAVPS RSSASVPKPA    60
PQPYPFTSSL STINYDEFPT MVFPSGQISQ ASALAPAPPQ VLPQAPAPAP APAMVSALAQ   120
APAPVPVLAP GPPQAVAPPA PKPTQAGEGT LSEALLQLQF DDEDLGALLG NSTDPAVFTD   180
LASVDNSEFQ QLLNQGIPVA PHTTEPMLME YPEAITRLVT GAQRPPDPAP APLGAPGLPN   240
GLLSGDEDFS SIADMDFSAL L                                            261

SEQ ID NO: 9            moltype = AA  length = 525
FEATURE                 Location/Qualifiers
REGION                  1..525
                        note = Synthetic Polypeptide
source                  1..525
                        mol_type = protein
                        organism = synthetic construct
SEQUENCE: 9
RADALDDFDL DMLGSDALDD FDLDMLGSDA LDDFDLDMLG SDALDDFDLD MLINSRSSGS    60
PKKKRKVGSQ YLPDTDDRHR IEEKRKRTYE TFKSIMKKSP FSGPTDPRPP PRRIAVPSRS   120
SASVPKPAPQ PYPFTSSLST INYDEFPTMV FPSGQISQAS ALAPAPPQVL PQAPAPAPAP   180
AMVSALAQAP APVPVLAPGP PQAVAPPAPK PTQAGEGTLS EALLQLQFDD EDLGALLGNS   240
TDPAVFTDLA SVDNSEFQQL LNQGIPVAPH TTEPMLMEYP EAITRLVTGA QRPPDPAPAP   300
LGAPGLPNGL LSGDEDFSSI ADMDFSALLG SGSGSRDSRE GMFLPKPEAG SAISDVFEGR   360
EVCQPKRIRP FHPPGSPWAN RPLPASLAPT PTGPVHEPVG SLTPAPVPQP LDPAPAVTPE   420
ASHLLEDPDE ETSQAVKALR EMADTVIPQK EEAAICGQMD LSHPPPRGHL DELTTTLESM   480
TEDLNLDSPL TPELNEILDT FLNDECLLHA MHISTGLSIF DTSLF                   525

SEQ ID NO: 10           moltype = AA  length = 239
FEATURE                 Location/Qualifiers
REGION                  1..239
                        note = Synthetic Polypeptide
source                  1..239
                        mol_type = protein
                        organism = synthetic construct
SEQUENCE: 10
MQENYKILVV DDDMRLRALL ERYLTEQGFQ VRSVANAEQM DRLLTRESFH LMVLDLMLPG    60
EDGLSICRRL RSQSNPMPII MVTAKGEEVD RIVGLEIGAD DYIPKPFNPR ELLARIRAVL   120
RRQANELPGA PSQEEAVIAF GKFKLNLGTR EMFREDEPMP LTSGEFAVLK ALVSHPREPL   180
SRDKLMNLAR GREYSAMERS IDVQISRLRR MVEEDPAHPR YIQTVWGLGY VFVPDGSKA    239

SEQ ID NO: 11           moltype = AA  length = 216
FEATURE                 Location/Qualifiers
REGION                  1..216
                        note = Synthetic Polypeptide
source                  1..216
                        mol_type = protein
                        organism = synthetic construct
SEQUENCE: 11
MSNQEPATIL LIDDHPMLRT GVKQLISMAP DITVVGEASN GEQGIELAES LDPDLILLDL    60
NMPGMNGLET LDKLREKSLS GRIVVFSVSN HEEDVVTALK RGADGYLLKD MEPEDLLKAL   120
HQAAAGEMVL SEALTPVLAA SLRANRATTE RDVNQLTPRE RDILKLIAQG LPNKMIARRL   180
DITESTVKVH VKHMLKKMKL KSRVEAAVWV HQERIF                             216

SEQ ID NO: 12           moltype = AA  length = 469
FEATURE                 Location/Qualifiers
REGION                  1..469
                        note = Synthetic Polypeptide
source                  1..469
                        mol_type = protein
                        organism = synthetic construct
SEQUENCE: 12
MQRGIVWVVD DDSSIRWVLE RALAGAGLTC TTFENGAEVL EALASKTPDV LLSDIRMPGM    60
DGLALLKQIK QRHPMLPVII MTAHSDLDAA VSAYQQGAFD YLPKPFDIDE AVALVERAIS   120
HYQEQQQPRN VQLNGPTTDI IGEAPAMQDV FRIIGRLSRS SISVLINGES GTGKELVAHA   180
LHRHSPRAKA PFIALNMAAI PKDLIESELF GHEKGAFTGA NTIRQGRFEQ ADGGTLFLDE   240
IGDMPLDVQT RLLRVLADGQ FYRVGGYAPV KVDVRIIAAT HQNLEQRVQE GKFREDLFHR   300
LNVIRVHLPP LRERREDIPR LARHFLQVAA RELGVEAKLL HPETEAALTR LAWPGNVRQL   360
ENTCRWLTVM AAGQEVLIQD LPGELFESTV AESTSQMQPD SWATLLAQWA DRALRSGHQN   420
LLSEAQPELE RTLLTTALRH TQGHKQEAAR LLGWGRNTLT RKLKELGME              469
```

```
SEQ ID NO: 13              moltype = AA   length = 229
FEATURE                    Location/Qualifiers
REGION                     1..229
                           note = Synthetic Polypeptide
source                     1..229
                           mol_type = protein
                           organism = synthetic construct
SEQUENCE: 13
MARRILVVED EAPIREMVCF VLEQNGFQPV EAEDYDSAVN QLNEPWPDLI LLDWMLPGGS  60
GIQFIKHLKR ESMTRDIPVV MLTARGEEED RVRGLETGAD DYITKPFSPK ELVARIKAVM 120
RRISPMAVEE VIEMQGLSLD PTSHRVMAGE EPLEMGPTEF KLLHFFMTHP ERVYSREQLL 180
NHVWGTNVYV EDRTVDVHIR RLRKALEPGG HDRMVQTVRG TGYRFSTRF            229

SEQ ID NO: 14              moltype = DNA   length = 21
FEATURE                    Location/Qualifiers
misc_feature               1..21
                           note = Synthetic Polynucleotide
source                     1..21
                           mol_type = other DNA
                           organism = synthetic construct
SEQUENCE: 14
atttacattt tgaaacatct a                                            21

SEQ ID NO: 15              moltype = DNA   length = 16
FEATURE                    Location/Qualifiers
misc_feature               1..16
                           note = Synthetic Polynucleotide
source                     1..16
                           mol_type = other DNA
                           organism = synthetic construct
SEQUENCE: 15
taccgctatt gaggta                                                  16

SEQ ID NO: 16              moltype = DNA   length = 17
FEATURE                    Location/Qualifiers
misc_feature               1..17
                           note = Synthetic Polynucleotide
source                     1..17
                           mol_type = other DNA
                           organism = synthetic construct
SEQUENCE: 16
tgcactaaaa tggtgca                                                 17

SEQ ID NO: 17              moltype = DNA   length = 18
FEATURE                    Location/Qualifiers
misc_feature               1..18
                           note = Synthetic Polynucleotide
misc_difference            9
                           note = w may be a or t
misc_difference            11
                           note = w may be a or t
misc_difference            18
                           note = y may be c or t
source                     1..18
                           mol_type = other DNA
                           organism = synthetic construct
SEQUENCE: 17
ctgtcatawa wctgtcay                                                18

SEQ ID NO: 18              moltype = DNA   length = 20
FEATURE                    Location/Qualifiers
misc_feature               1..20
                           note = Synthetic Polynucleotide
source                     1..20
                           mol_type = other DNA
                           organism = synthetic construct
SEQUENCE: 18
tttgtattca gcccatatcg                                              20

SEQ ID NO: 19              moltype = DNA   length = 22
FEATURE                    Location/Qualifiers
misc_feature               1..22
                           note = Synthetic Polynucleotide
source                     1..22
                           mol_type = other DNA
                           organism = synthetic construct
SEQUENCE: 19
aacgatatgg gctgaataca aa                                           22
```

```
SEQ ID NO: 20            moltype = DNA   length = 21
FEATURE                  Location/Qualifiers
misc_feature             1..21
                         note = Synthetic Polynucleotide
source                   1..21
                         mol_type = other DNA
                         organism = synthetic construct
SEQUENCE: 20
tttaattaaa gacttcaagc g                                                 21

SEQ ID NO: 21            moltype = DNA   length = 22
FEATURE                  Location/Qualifiers
misc_feature             1..22
                         note = Synthetic Polynucleotide
source                   1..22
                         mol_type = other DNA
                         organism = synthetic construct
SEQUENCE: 21
ccgcttgaag tctttaatta aa                                                22

SEQ ID NO: 22            moltype = DNA   length = 20
FEATURE                  Location/Qualifiers
misc_feature             1..20
                         note = Synthetic Polynucleotide
source                   1..20
                         mol_type = other DNA
                         organism = synthetic construct
SEQUENCE: 22
taattgtcaa atcagagtgc                                                   20

SEQ ID NO: 23            moltype = DNA   length = 22
FEATURE                  Location/Qualifiers
misc_feature             1..22
                         note = Synthetic Polynucleotide
source                   1..22
                         mol_type = other DNA
                         organism = synthetic construct
SEQUENCE: 23
aagcactctg atttgacaat ta                                                22

SEQ ID NO: 24            moltype = DNA   length = 20
FEATURE                  Location/Qualifiers
misc_feature             1..20
                         note = Synthetic Polynucleotide
source                   1..20
                         mol_type = other DNA
                         organism = synthetic construct
SEQUENCE: 24
tttatgagga atctctttgg                                                   20

SEQ ID NO: 25            moltype = DNA   length = 22
FEATURE                  Location/Qualifiers
misc_feature             1..22
                         note = Synthetic Polynucleotide
source                   1..22
                         mol_type = other DNA
                         organism = synthetic construct
SEQUENCE: 25
aaccaaagag attcctcata aa                                                22

SEQ ID NO: 26            moltype = DNA   length = 20
FEATURE                  Location/Qualifiers
misc_feature             1..20
                         note = Synthetic Polynucleotide
source                   1..20
                         mol_type = other DNA
                         organism = synthetic construct
SEQUENCE: 26
ttcgaagtat tccgcgtacg                                                   20

SEQ ID NO: 27            moltype = DNA   length = 22
FEATURE                  Location/Qualifiers
misc_feature             1..22
                         note = Synthetic Polynucleotide
source                   1..22
                         mol_type = other DNA
                         organism = synthetic construct
SEQUENCE: 27
cacgtacgcg gaatacttcg aa                                                22
```

```
SEQ ID NO: 28          moltype = DNA  length = 21
FEATURE                Location/Qualifiers
misc_feature           1..21
                       note = Synthetic Polynucleotide
source                 1..21
                       mol_type = other DNA
                       organism = synthetic construct
SEQUENCE: 28
atttacattt tgaaacatct a                                                   21

SEQ ID NO: 29          moltype = DNA  length = 16
FEATURE                Location/Qualifiers
misc_feature           1..16
                       note = Synthetic Polynucleotide
source                 1..16
                       mol_type = other DNA
                       organism = synthetic construct
SEQUENCE: 29
taccgctatt gaggta                                                         16

SEQ ID NO: 30          moltype = DNA  length = 17
FEATURE                Location/Qualifiers
misc_feature           1..17
                       note = Synthetic Polynucleotide
source                 1..17
                       mol_type = other DNA
                       organism = synthetic construct
SEQUENCE: 30
tgcactaaaa tggtgca                                                        17

SEQ ID NO: 31          moltype = DNA  length = 18
FEATURE                Location/Qualifiers
misc_feature           1..18
                       note = Synthetic Polynucleotide
misc_difference        9
                       note = w may be a or t
misc_difference        11
                       note = w may be a or t
misc_difference        18
                       note = y may be c or t
source                 1..18
                       mol_type = other DNA
                       organism = synthetic construct
SEQUENCE: 31
ctgtcatawa wctgtcay                                                       18
```